(12) United States Patent
Ritter

(10) Patent No.: US 11,737,739 B2
(45) Date of Patent: Aug. 29, 2023

(54) DENTAL INSTRUMENT ASSEMBLIES AND COMPONENTS FOR USE WITHIN DENTAL INSTRUMENT ASSEMBLIES

(71) Applicant: Ascentcare Dental Products, Inc., Grand Haven, MI (US)

(72) Inventor: Austin R. Ritter, Grand Haven, MI (US)

(73) Assignee: Ascentcare Dental Products, Inc., Grand Haven, MI (US)

(*) Notice: Subject to any disclaimer, the term of this patent is extended or adjusted under 35 U.S.C. 154(b) by 0 days.

(21) Appl. No.: 17/209,042

(22) Filed: Mar. 22, 2021

(65) Prior Publication Data
US 2021/0204923 A1  Jul. 8, 2021

Related U.S. Application Data

(63) Continuation-in-part of application No. 15/959,238, filed on Apr. 22, 2018, now Pat. No. 10,952,707, which is a continuation of application No. 15/133,555, filed on Apr. 20, 2016, now Pat. No. 9,968,341, said application No. 15/959,238 is a continuation-in-part of application No. 15/807,465, filed on Nov. 8, 2017, now Pat. No. 10,350,027.
(Continued)

(51) Int. Cl.
| | |
|---|---|
| *A61B 1/06* | (2006.01) |
| *A61B 13/00* | (2006.01) |
| *A61C 1/08* | (2006.01) |
| *A61C 17/08* | (2006.01) |
| *A61B 1/24* | (2006.01) |
| *A61B 1/32* | (2006.01) |
| *A61B 90/16* | (2016.01) |

(52) U.S. Cl.
CPC ............... *A61B 13/00* (2013.01); *A61B 1/06* (2013.01); *A61B 1/24* (2013.01); *A61B 1/32* (2013.01); *A61C 1/088* (2013.01); *A61C 17/08* (2019.05); *A61B 90/16* (2016.02)

(58) Field of Classification Search
CPC ............ A61B 13/00; A61B 1/32; A61C 17/08
USPC .......................................................... 385/57
See application file for complete search history.

(56) References Cited

U.S. PATENT DOCUMENTS

| | | | | |
|---|---|---|---|---|
| 3,636,633 | A * | 1/1972 | Fuller | A61G 15/14 433/29 |
| 5,634,790 | A * | 6/1997 | Pathmanabhan | A61B 1/0607 433/29 |
| 10,561,310 | B2 * | 2/2020 | Lutz | A61B 1/247 |

FOREIGN PATENT DOCUMENTS

| | | | | |
|---|---|---|---|---|
| CA | 2286230 | A1 * | 10/1998 | |
| CA | 2349301 | C  * | 3/2007 | ......... A61B 1/00103 |
| CN | 1299251 | A  * | 6/2001 | ............. A61C 1/088 |

* cited by examiner

*Primary Examiner* — Kaveh C Kianni
(74) *Attorney, Agent, or Firm* — Bodman PLC

(57) ABSTRACT

Dental instrument assemblies (e.g., mouth pieces, bite blocks, vacuum dental mirrors, illuminated dental mirrors, illuminated dental wedges, trans-illumination dental instrument, illuminated dental bite blocks, etc.) are provided. The dental instrument assemblies may be adapted to be periodically sterilized. The dental instrument assemblies may include a magnetically energetic fiber optic coupler. The magnetically energetic fiber optic coupler may be configured to allow dental instrument adapter to rotate with respect to an associated fiber optic cable that is removably connected to the magnetically energetic fiber optic coupler. The dental instrument assemblies may include a fiber optic material that is encapsulated.

16 Claims, 15 Drawing Sheets

Related U.S. Application Data

(60) Provisional application No. 62/150,448, filed on Apr. 21, 2015, provisional application No. 62/422,669, filed on Nov. 16, 2016, provisional application No. 62/422,927, filed on Nov. 16, 2016, provisional application No. 62/423,607, filed on Nov. 17, 2016.

DENTAL INSTRUMENT ASSEMBLIES AND COMPONENTS FOR USE WITHIN DENTAL INSTRUMENT ASSEMBLIES

CROSS-REFERENCE TO RELATED APPLICATIONS AND CLAIM TO PRIORITY

The present application is a continuation-in-part of U.S. patent application Ser. No. 15/959,238, entitled OPTICAL FIBER COUPLERS AND COMPONENTS FOR USE IN OPTICAL FIBER COUPLERS, filed Apr. 22, 2018, the entire disclosure of which is incorporated herein by reference.

U.S. patent application Ser. No. 15/959,238 is a continuation of U.S. patent application Ser. No. 15/133,555, entitled DENTAL BITE BLOCK ASSEMBLY, filed Apr. 20, 2016; and is a continuation-in-part of U.S. patent application Ser. No. 15/807,465, entitled ILLUMINATED DENTAL INSTRUMENT ASSEMBLIES AND COMPONENTS FOR USE WITHIN ILLUMINATED DENTAL INSTRUMENT ASSEMBLIES, filed Nov. 8, 2017, the entire disclosures of which are incorporated herein by reference. U.S. patent application Ser. No. 15/133,555 claims priority under 35 U.S.C. § 119(e) of U.S. Provisional Application Ser. No. 62/150,448, entitled Dental Bite Block Assembly, filed Apr. 21, 2015, the entire disclosure of which is incorporated herein by reference. U.S. patent application Ser. No. 15/807,465 claims priority under 35 U.S.C. § 119(e) of U.S. Provisional Application Ser. No. 62/422,669, entitled Magnetically Coupled Fiber Optic Lighted Dental Mirror, filed Nov. 16, 2016; 62/422,927, entitled Magnetically Coupled Fiber Optic Tooth Illumination Pick Light Tool for Dentistry, filed Nov. 16, 2016; and 62/423,607, entitled Illuminated Dental Wedge, filed Nov. 17, 2016; the entire disclosures of which are incorporated herein by reference.

TECHNICAL FIELD

The present disclosure generally relates to dental instrument assemblies (e.g., vacuum valves, illumination and vacuum adaptors, illuminated dental mirrors, illuminated dental wedges, illuminated dental picks, illuminated dental bite blocks, vacuum dental mirrors, illuminated vacuum dental mirrors, illuminated vacuum mouth pieces, etc.), and components for use within illuminated dental mirror assemblies. More particularly, the present disclosure relates to dental instrument assemblies that are adapted to be periodically sterilized.

BACKGROUND

Dental procedures and/or examinations often require a dentist and/or dental hygienist to work under numerous limitations, primarily among them being restricted physical access available for performing dental procedures within a patient's mouth and limited ambient light. For example, during dental procedures, the patient's mouth must often times receive a dental hand instrument, a dental drill unit, a saliva ejection tube to evacuate particulates and/or saliva from the patient's mouth during the dental procedure, which typically require assistance of a another person, such as a dental assistant. In addition, use of dental accessories (e.g., light sources, tongue depressors, vacuum mouth pieces, illuminated mouth pieces, vacuum mouth pieces with bite block, illuminated vacuum mouth with bite block, dental mirrors, etc.) is occasionally required.

Use of optoelectronic devices having external light sources (e.g., an overhead light source, a dentist head-mounted light source, etc.) require alignment of the external light source and/or the patient's head to be periodically adjusted during a dental procedure. Periodic realignment of either the patient's head or an external light source often requires the dentist to be distracted and, is at best, cumbersome. Frequently, dental instruments, used during dental procedures, often block or create shadows that prohibit external light from reaching an associated mirror and/or a work area needing light to aid in the procedure being performed.

Prior attempts to introduce a light source, that emit light or provide luminous emittance from inside the patient's mouth, add further obstruction and/or limit access for performance of dental procedures and typically required use of two hands, or a dental assistant, to attach or remove the light source. Known illuminated dental mirrors include light sources that generate unacceptable heat. Moreover, prior attempts to introduce an inter-oral light source, from which the light is emitted, from within a patient's mouth have not accounted for the need to periodically sterilize the light source after every use.

Prior attempts to introduce illuminated dental instruments inside a patient's mouth included associated instruments having rough surfaces and/or couplers with crevices to which bacteria and blood attached. Prior attempts also failed to project high enough LUX with an acceptable color temperature (Kelvin) to aid in trans-illumination of teeth for assistance in diagnoses. Furthermore, attempts to use a lighted dental mirror for long periods of time or hours of continuous use in a dental practice each and every day have been cost prohibitive and unreliable. Hence, an illuminated dental instrument (e.g., an illuminated dental mirror, an illuminated dental wedge, an illuminated dental bite block, an illuminated dental pick, etc.) assembly which overcomes these drawbacks would be advantageous.

SUMMARY OF THE INVENTION

A dental instrument assembly may include a dental instrument adapter having an illumination source connection, a vacuum source connection, and a dental instrument connection. The vacuum source connection may be swivably connectable to a vacuum source. The illumination source connection may be swivably connectable to an illumination source independent of the vacuum source connection to the vacuum source. The dental instrument connection may be connectable to a removable dental instrument.

In another embodiment, a dental instrument may include a dental instrument having at least one receptacle configured to receive a respective adapter interlock of a dental instrument adapter. The dental instrument may be a mouth piece having a first front flap, a second front flap, a first rear flap, and a second rear flap. A front perimeter around an outer edge of the first front flap and an outer edge of the second front flap may be less than a rear perimeter around an outer edge of the first rear flap and an outer edge of the second rear flap.

In a further embodiment, a dental instrument assembly may include a dental instrument having an integral bite block. The dental instrument may be a mouth piece having a first front flap, a second front flap, a first rear flap, and a second rear flap. A front perimeter around an outer edge of the first front flap and an outer edge of the second front flap is less than a rear perimeter around an outer edge of the first rear flap and an outer edge of the second rear flap.

An illuminated dental instrument assembly may include a fiber optic cable coupler including a magnetically energetic material. The fiber optic cable coupler may be configured to allow the illuminated dental instrument assembly to rotate with respect to an associated fiber optic cable. The illuminated dental mirror may also include a handle that at least partially encapsulates a fiber optic element within a handle material that does not degrade when sterilized in an autoclave. An illuminated dental instrument assembly may include smooth surfaces and light couplers free of crevices, such that bacteria and blood may not attach to the illuminated dental instrument assembly.

An illuminated dental instrument assembly may include an axially magnetized linear fiber optic coupling system. An axially magnetized linear fiber optic coupler may reduce binding and allow quick and easy engagement (e.g., may only require one hand of a user). An axially magnetized linear fiber optic coupler may reduce, or eliminate, associated wear. An illuminated dental instrument assembly may project high enough LUX with an acceptable color temperature (Kelvin) to aid in trans-illumination of teeth for assistance in diagnoses.

In another embodiment, an illuminated dental instrument assembly may include a fiber optic cable coupler. The fiber optic cable coupler may be configured to allow the illuminated dental instrument assembly to rotate with respect to an associated fiber optic cable. The illuminated dental mirror may also include a handle that at least partially encapsulates a fiber optic element within a handle material that does not degrade when sterilized in an autoclave.

In a further embodiment, an illuminated dental instrument assembly may include a fiber optic cable coupler including a magnetically energetic material. The fiber optic cable coupler may be configured to allow the illuminated dental instrument assembly to rotate with respect to an associated fiber optic cable. The illuminated dental mirror may also include a handle having a fiber optic element extending from a proximal end of the handle to a distal end of the handle.

These and other aspects, objects, and features of the present invention will be understood and appreciated by those skilled in the art upon studying the following specification, claims, and appended drawings.

DETAILED DESCRIPTION

Figure 1:
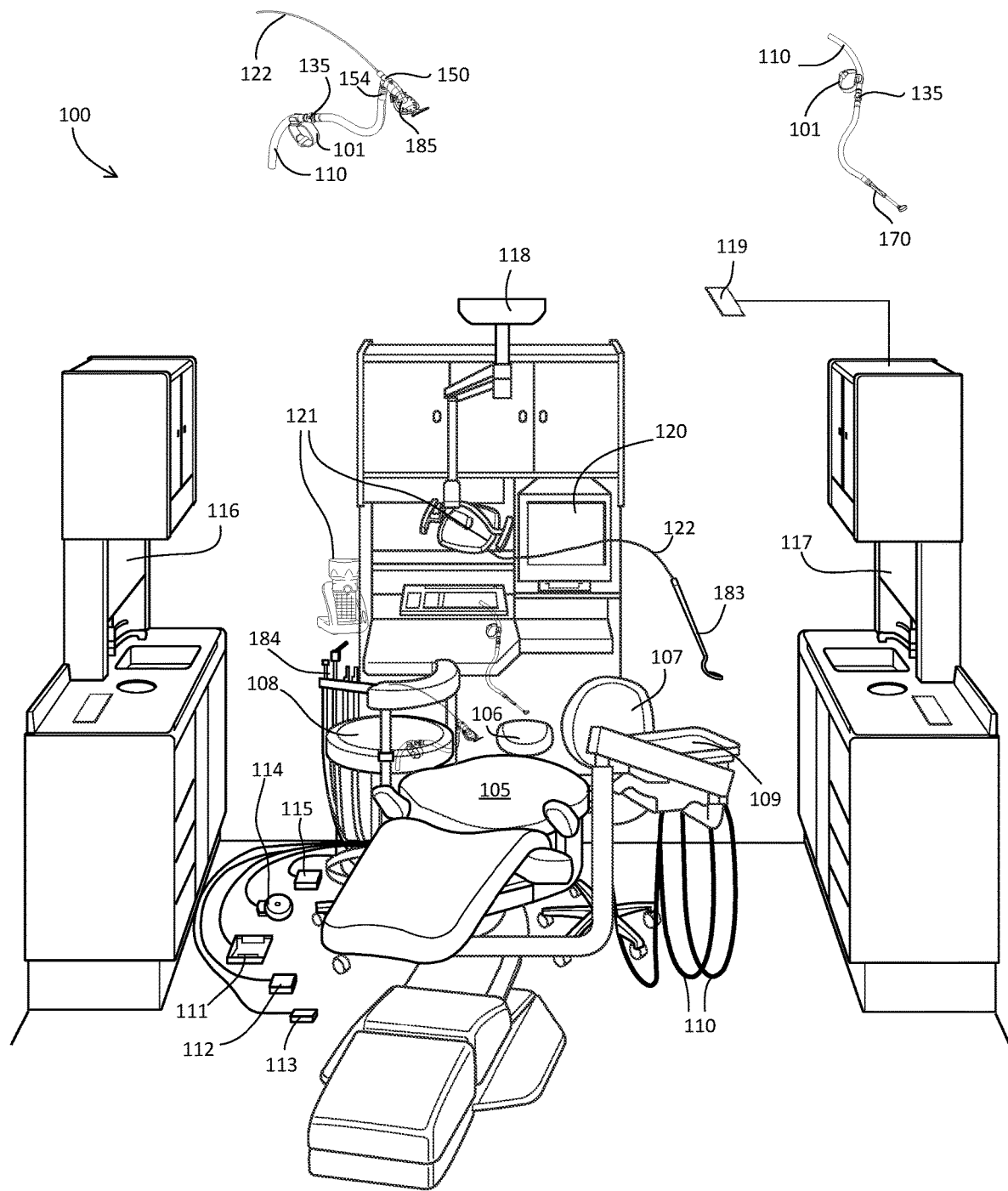
FIG. 1 depicts various example dental instrument assemblies within a dental examination/operatory room.

Dental instrument assemblies are provided that may incorporate both saliva evacuation and inter-oral illumination. The associated dental instruments and components for use within the dental instrument assemblies may be sterilizable without destruction. For example, the dental instruments and components for use within the dental instrument assemblies may be sterilizable in an autoclave at 121° C. for at least 30 minutes by using saturated steam under at least 15 psi.

Illuminated mouth pieces and components for use within illuminated dental instrument assemblies are provided. The illuminated dental instrument assemblies may be sterilized in, for example, an autoclave or a chemical solution after use with each given patient. The illuminated dental instrument assembly components may include materials that withstand exposure to high temperatures (e.g., temperatures in excess of 121° C. Exterior components of the illuminated dental instrument assemblies may include materials that withstand exposure to high temperatures and chemicals used for sterilization.

An illumination source may be communicatively connected to an illuminated dental instrument assembly via, for example, a fiber optic cable via at least one rotatable fiber optic coupler. The rotatable fiber optic coupler may be a magnetic light coupler (e.g., a magnetic light coupler as disclosed in commonly assigned U.S. Patent Application Publication No. 20160310234). The fiber optic cable may include a magnetic light coupler on each end (i.e., a first magnetic light coupler may connect to the light source and a second magnetic light coupler may connect to the illuminated dental mirror assembly).

As described in detail herein, an illuminated dental instrument may include a fiber optic element and extending between a magnetic light coupler on a first end of the handle to an optic element on a second end of the illuminated dental instrument. The fiber optic element may be encapsulated within other materials that may provide rigidity and/or isolation from an environment surrounding the illuminated dental instrument assembly (e.g., a dentist's hands, a dental assistant's hands, an interior of a dental patient's mouth, chemical sterilization, an autoclave, etc.). A fiber optic element may convey, and an illuminated dental instrument assembly may emit, for example, 80,000 LUX within a mouth of a patient.

As referenced in the figures, the same reference numerals may be used herein to refer to the same parameters and components or their similar modifications and alternatives. For purposes of description herein, the terms "upper," "lower," "right," "left," "rear," "front," "vertical," "horizontal," and derivatives thereof shall relate to the claimed invention as oriented in FIG. 1. However, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise. The drawings referenced herein are schematic and associated views thereof are not necessarily drawn to scale.

Turning to FIG. 1, a dental examination/operatory room 100 may include an illuminated dental mirror 183 interconnected with a light source 121 (e.g., a reorientable overhead light source, an independent light source, etc.) via, for example, a fiber optic cable 122. A light source 121 may include, for example, a light engine (e.g., Model No. HYLUX-STM-B, as available from Ascentcare Dental, Inc., Nunica, Mich., any light source as disclosed in commonly assigned U.S. Patent Application Publication No.

20160310234, a light emitting diode (LED) light source generally, a vertical cavity surface emitting laser (VCSEL) light source, a laser light source, a single-mode laser, Laser Light for Lighting, available from Kyocera-SLD Laser (kyocera-sldlaser.com), etc.). The fiber optic cable 122 may be similar to, for example, a fiber optic cable as disclosed in commonly assigned U.S. Patent Application Publication No. 20160310234, along with associated magnetic couplings. The fiber optic cable 122 may include, for example, a polymethyl methacrylate (PMMA) material (e.g., ESKA P/N: GHEV4002). The fiber optic cable 122 may have a refractive index of, for example, 1.49. The fiber optic cable 122 may have a transmission loss of, for example, approximately 170 dB/km. The fiber optic cable 122 may have a bandwidth of, for example, 40 MHz. The fiber optic cable 122 may have a temperature range of, for example, $-55°$ C. to $95°$ C. Associated magnetic light couplers (not shown in FIG. 1) may be similar to, for example, a magnetic light coupler as disclosed in commonly assigned U.S. Patent Application Publication No. 20160310234. In fact, the light source 121, the fiber optic cable 122, and magnetic light couplers may be similar to the light delivery system as disclosed in commonly assigned U.S. Patent Application Publication No. 20160310234.

The dental operator room 100 may include a reorientable dental patient chair 105 having a headrest 106, a dentist assistant chair 107, a dentist assistant tray 109 with vacuum sources 110, a dentist chair 108 having a dental instrument rack 184, a dentist station 116, a dental assistant station 117, a plurality of foot operated switches 111-115, an overhead support structure 118, at least one wireless battery charger/wireless communication hub 119 (e.g., an infrared charger/transponder, an electromagnetic charger/transponder, etc.), and a desktop computer 120. The wireless battery charger 119 may be, for example, KIIK as provided by WI-CHARGE LTD., 3 Pekeris St. Rehovot, 7670203, Israel, having a total number of clients 1-50, 24 Wh/day, a total delivered power of 500 mW, a field of view of $100°/100\ m^2$, a maximum transmission distance of 10 m, an output voltage of 5V configurable, and embedded energy storage (e.g., super-capacitor/rechargeable battery). Alternatively, the wireless battery charger/transponder 119 may, for example, include a KIIK, as provided by WI-CHARGE LTD., 3 Pekeris St. Rehovot, 7670203, Israel, having a number of clients 1-10, a total delivered power of 1000 mW, a field of view of $100°/100\ m^2$, a maximum transmission distance of 8 m, an output voltage of 5V configurable, and embedded energy storage (e.g., super-capacitor/rechargeable battery). A first one of the plurality of foot operated switches 111-115 may be configured to, for example, activate the wireless battery charger/transponder 119. The wireless battery charger 119/transponder may charge a battery within, for example, a light engine 121.

The dentist station 116 and/or the dental assistant station 117 may include a light source 121 and an associated magnetic light coupler. A second one of the plurality of foot operated switches 111-115 may be configured to, for example, activate a first light source 121 (e.g., a visible light emitter 500-700 nm). A third one of the plurality of foot operated switches 111-115 may be configured to, for example, activate a second light source 121 (e.g., a blue light emitter, a ultra-violate C light emitter). The visible light emitter may be used to, for example, illuminate an interior of a dental patient's mouth. The blue light (e.g., 380-500 nm, 225-360 nm, 280-315 nm, 315-400 nm, a light emitter with a user adjustable wavelength emission, a light emitter with a user adjustable intensity, any sub-combination thereof, a combination thereof, etc.) emitter may be used to, for example, cure an associated blue light curable dental product (e.g., an adhesive, a filler, etc.) and/or disinfect an area proximate a dentist, a dental assistant, a patient, a sub-combination thereof, or a combination thereof.

A forth one of the plurality of foot operated switches 111-115 may control a pneumatically operated dental instrument. A fifth one of the plurality of foot operated switches 111-115 may control a vacuum source to control, for example, a saliva (liquid, debris, etc.) ejection element of a dental instrument assembly. For example, a dental instrument assembly may include a vacuum valve 135 and a fiber optic connection 122 functionally interconnected to a mouth piece 185 via a dental instrument adapter 150. Further details of these dental instrument assemblies and components for use within these dental instrument assemblies are described herein.

Figure 2B:
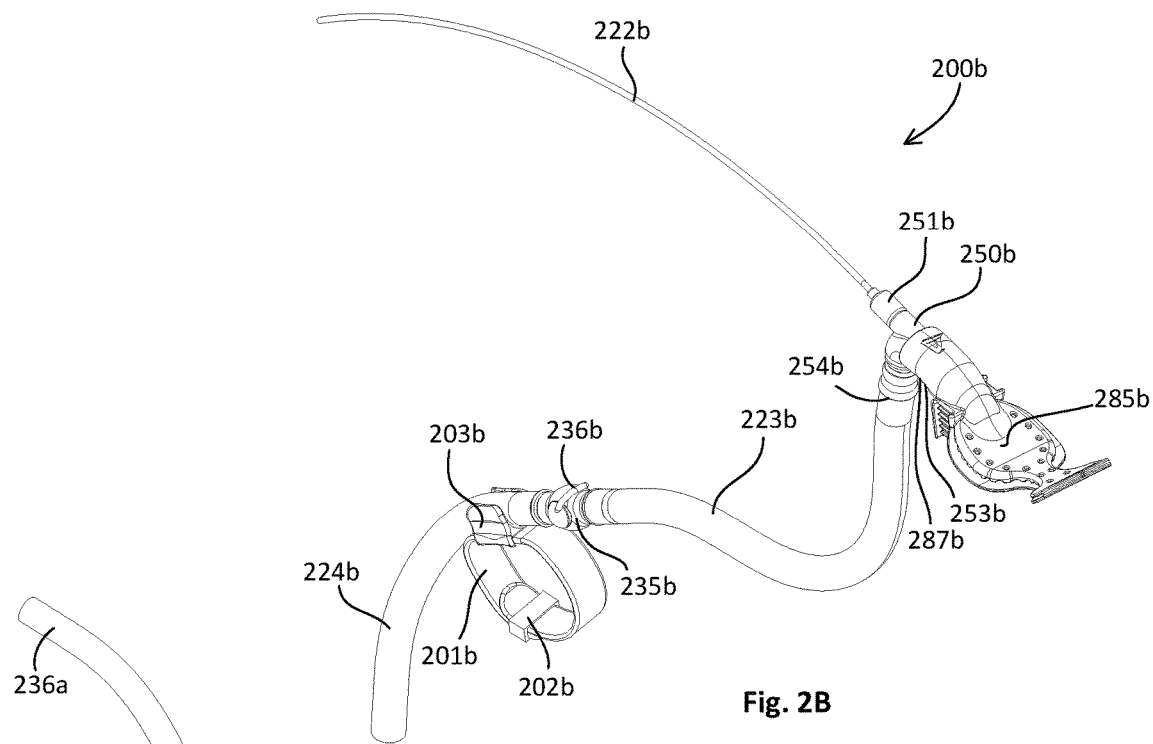
FIGS. 2A and 2B depict example dental instrument assemblies with illumination and/or saliva evacuation.
Figure 2A:
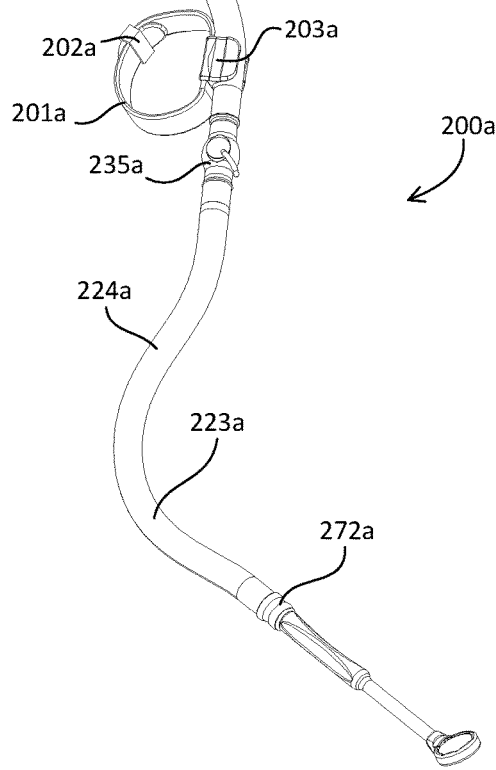
Figure 3A:
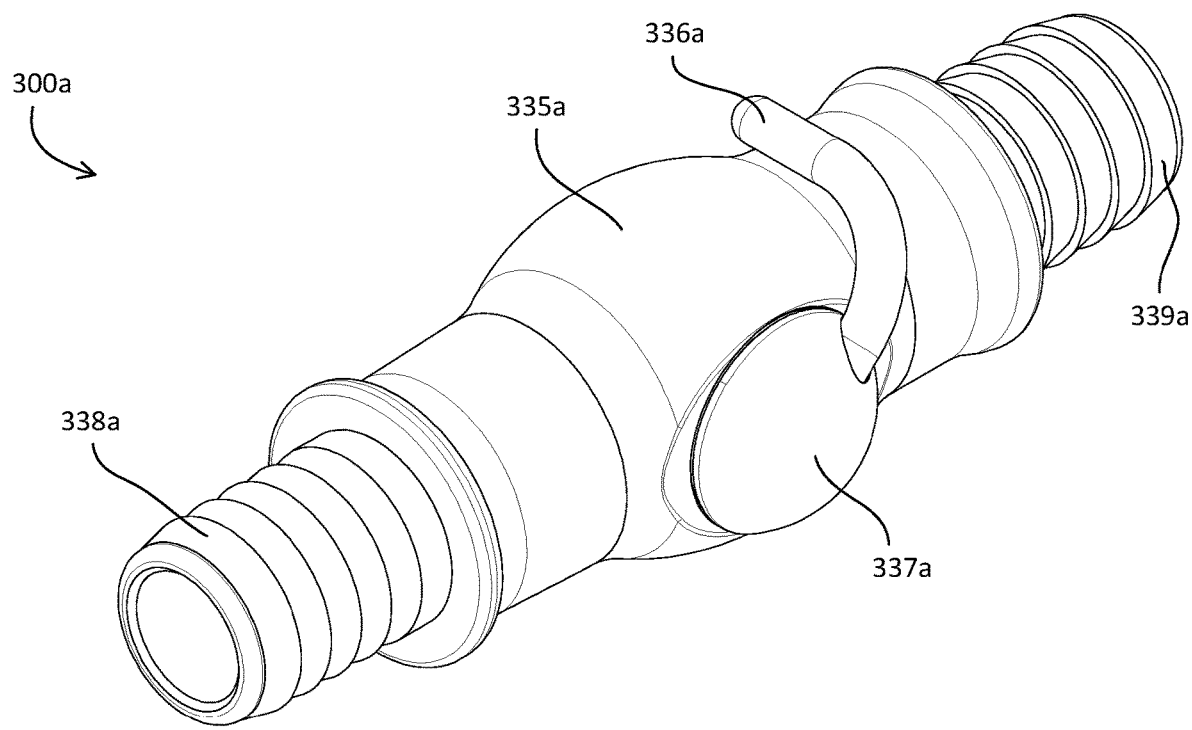
FIGS. 3A-D depict various views of an example valve assembly.
Figure 3B:
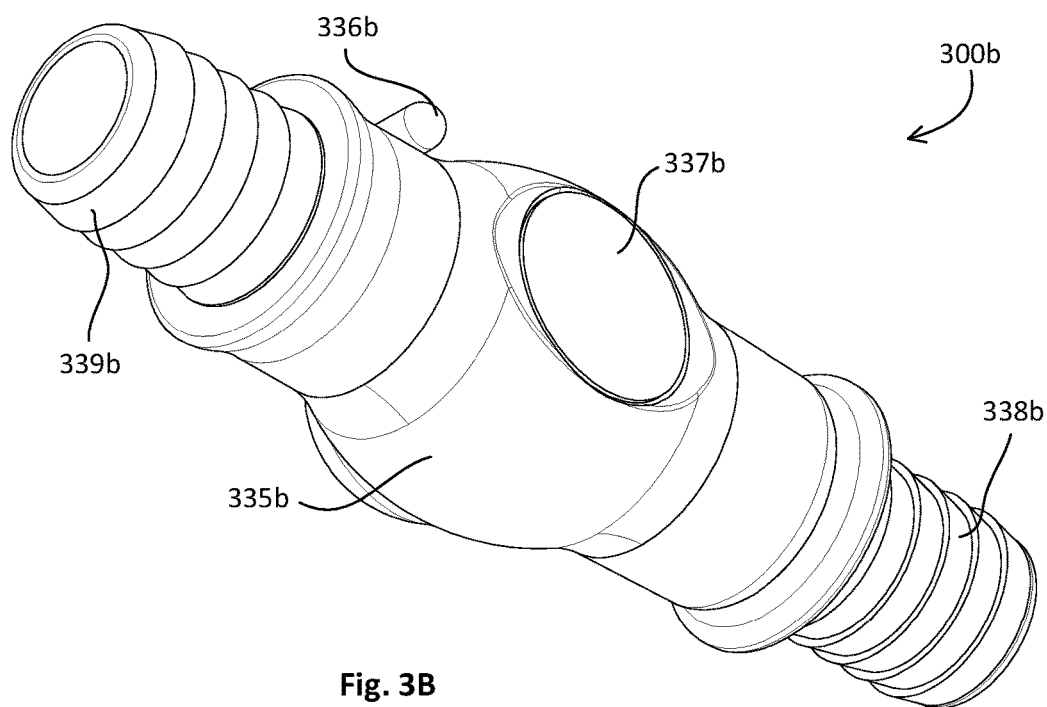
Figure 3C:
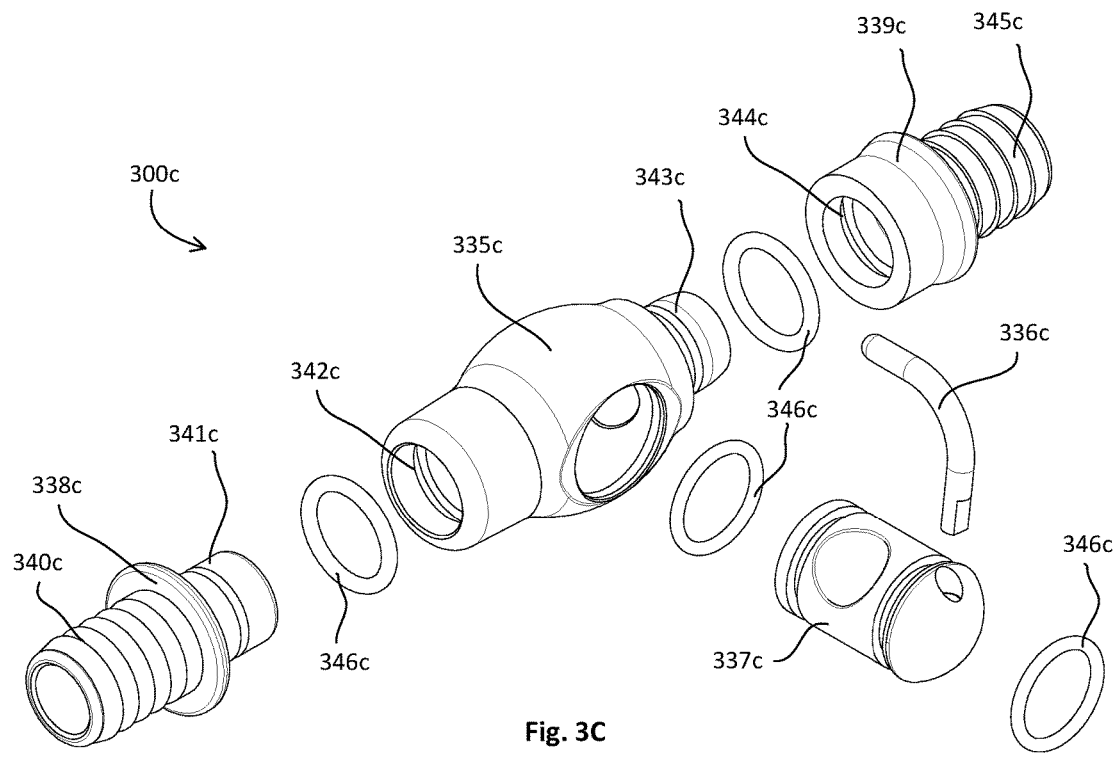
Figure 3D:
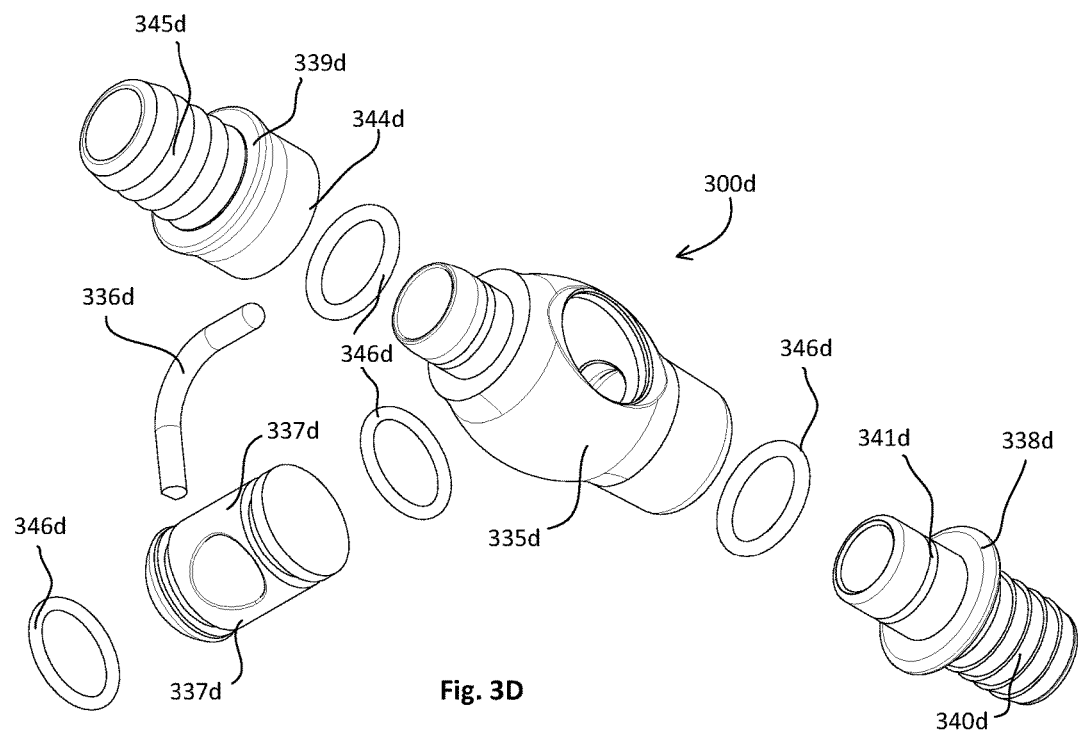
Figure 4A:
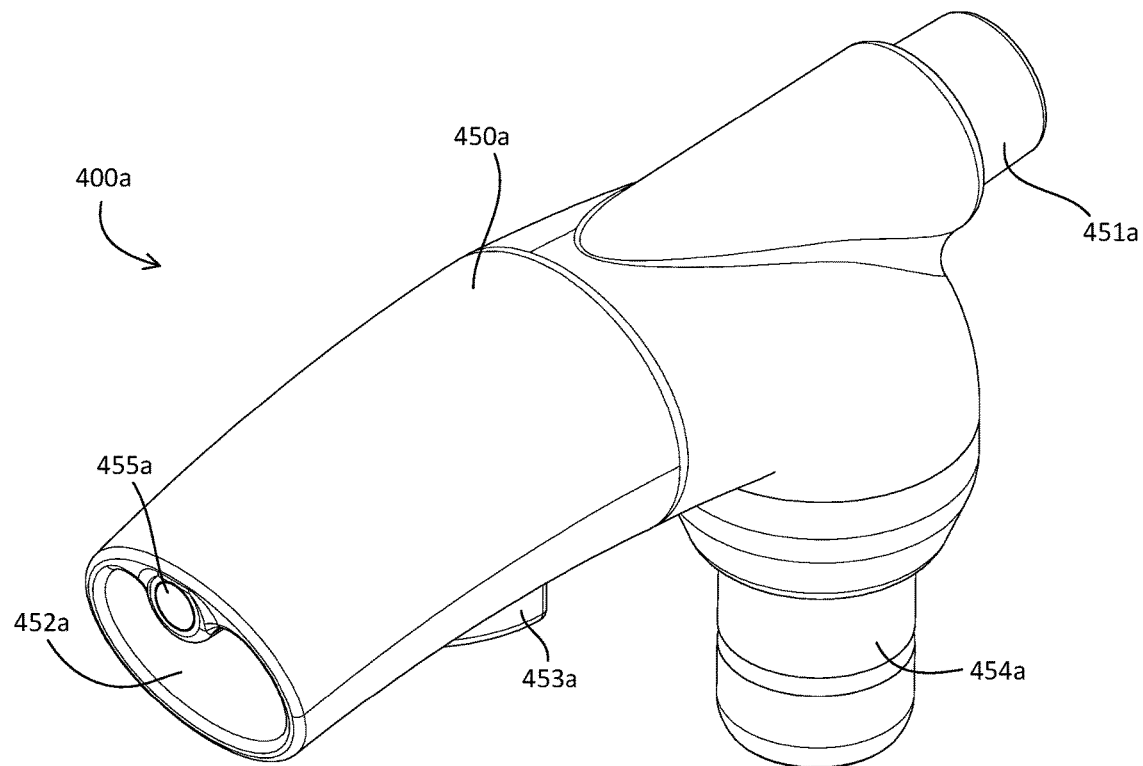
FIGS. 4A-H, 4J-N, 4P and 4Q depict various views of an example dental instrument adapter.
Figure 4B:
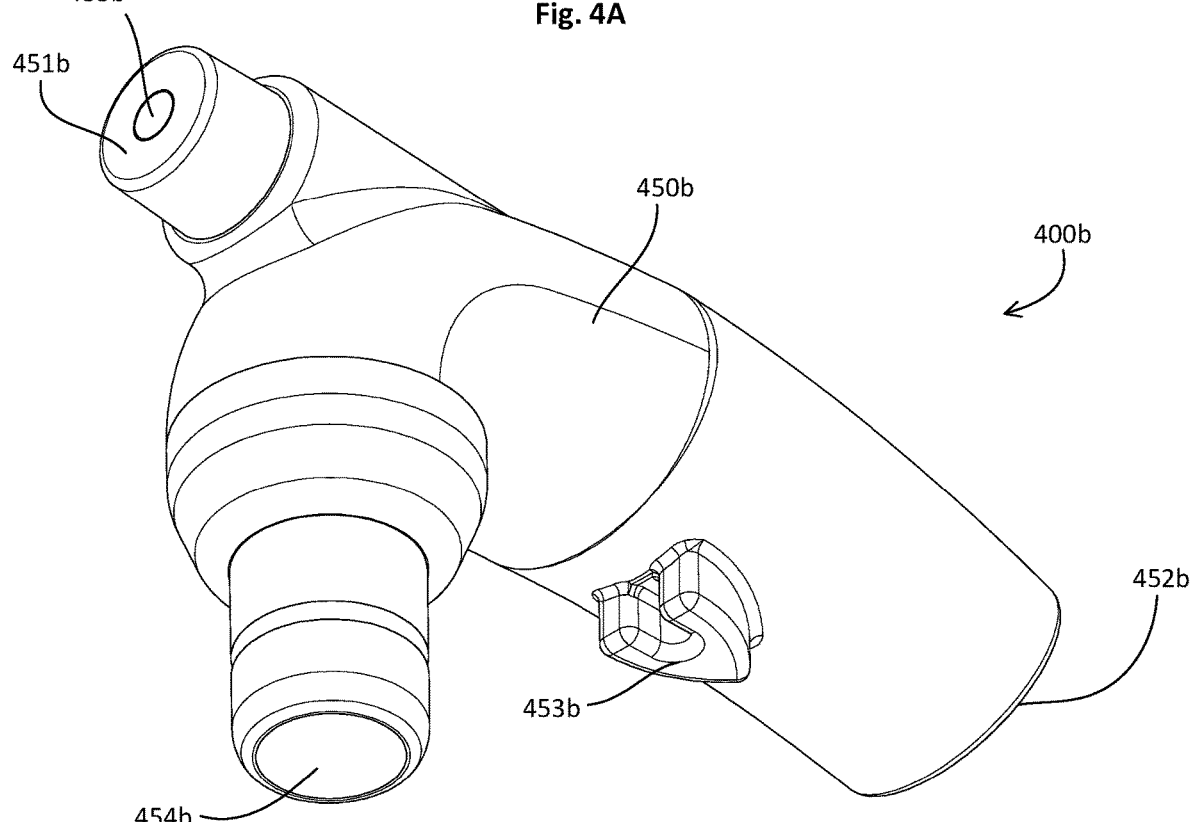
Figure 4C:
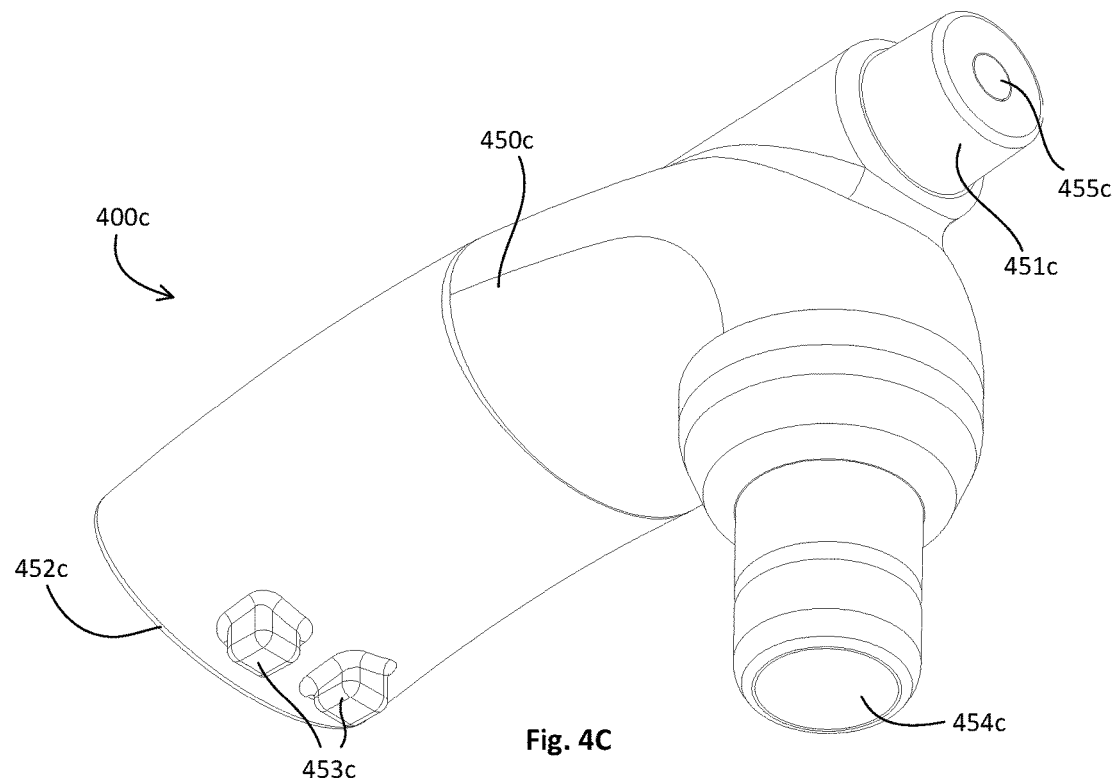
Figure 4D:
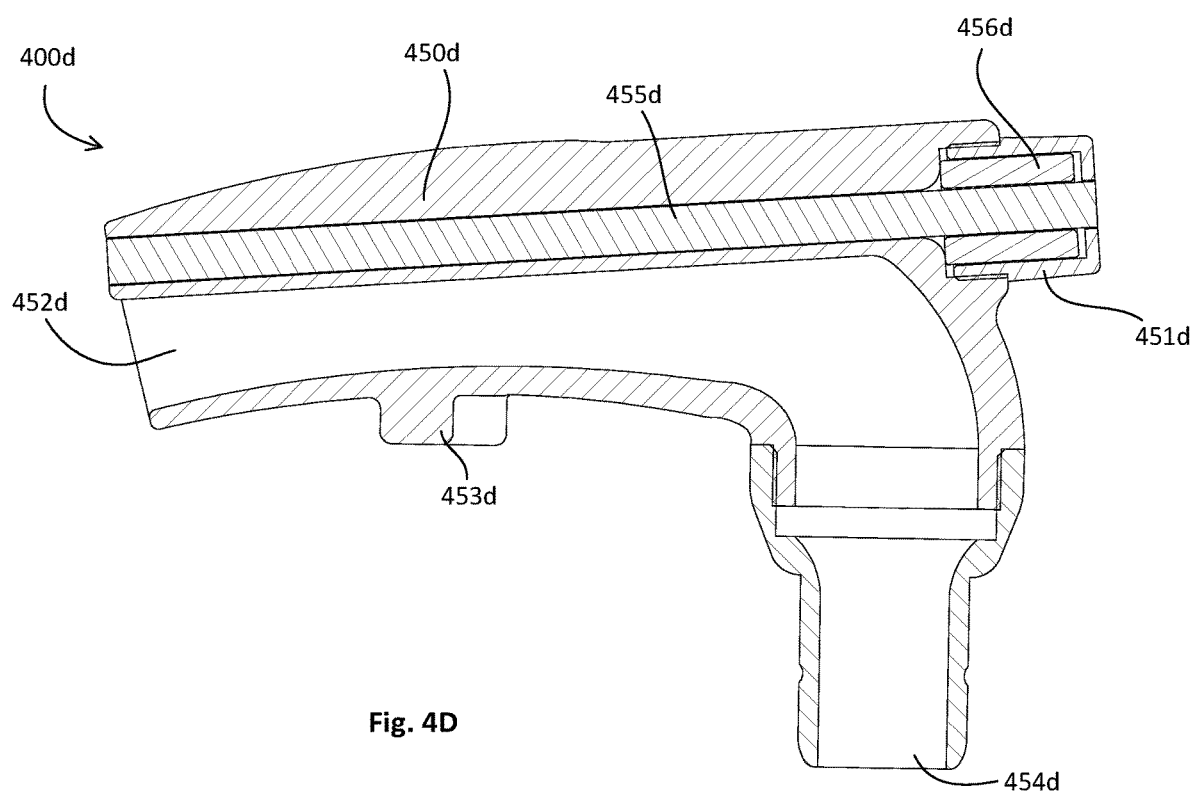
Figure 4E:
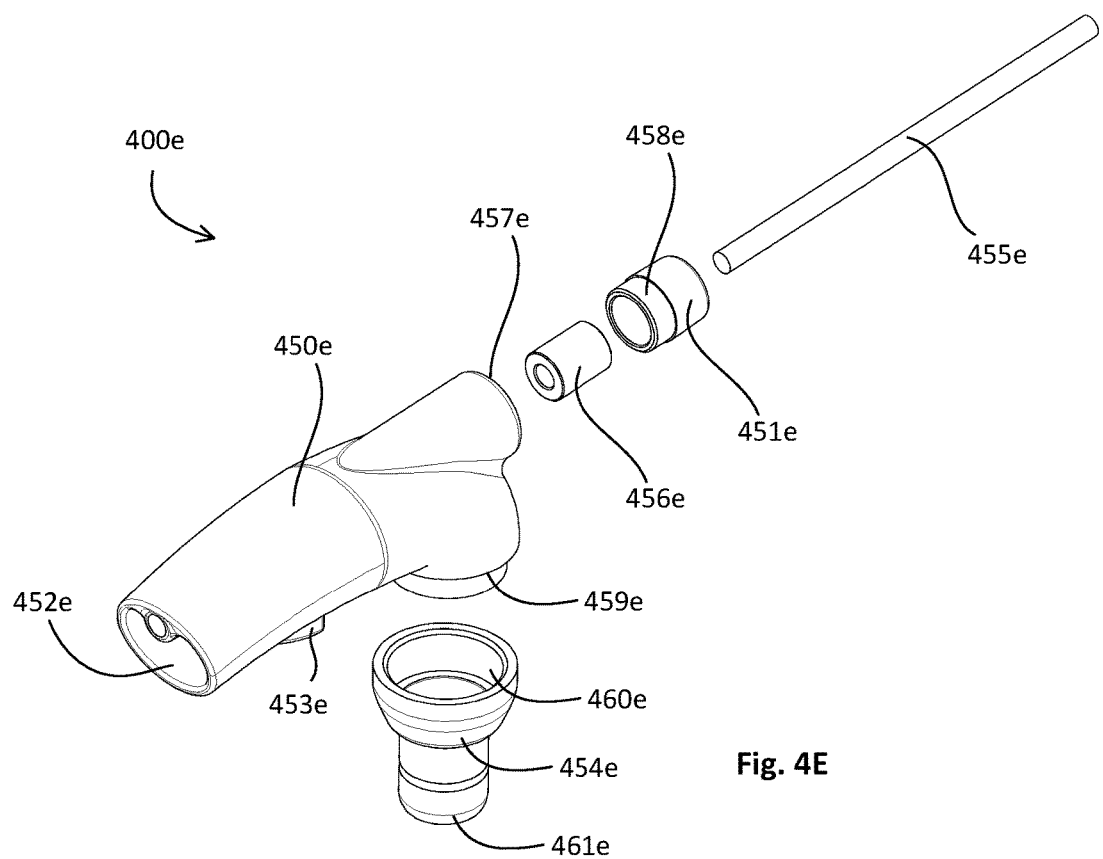
Figure 4F:
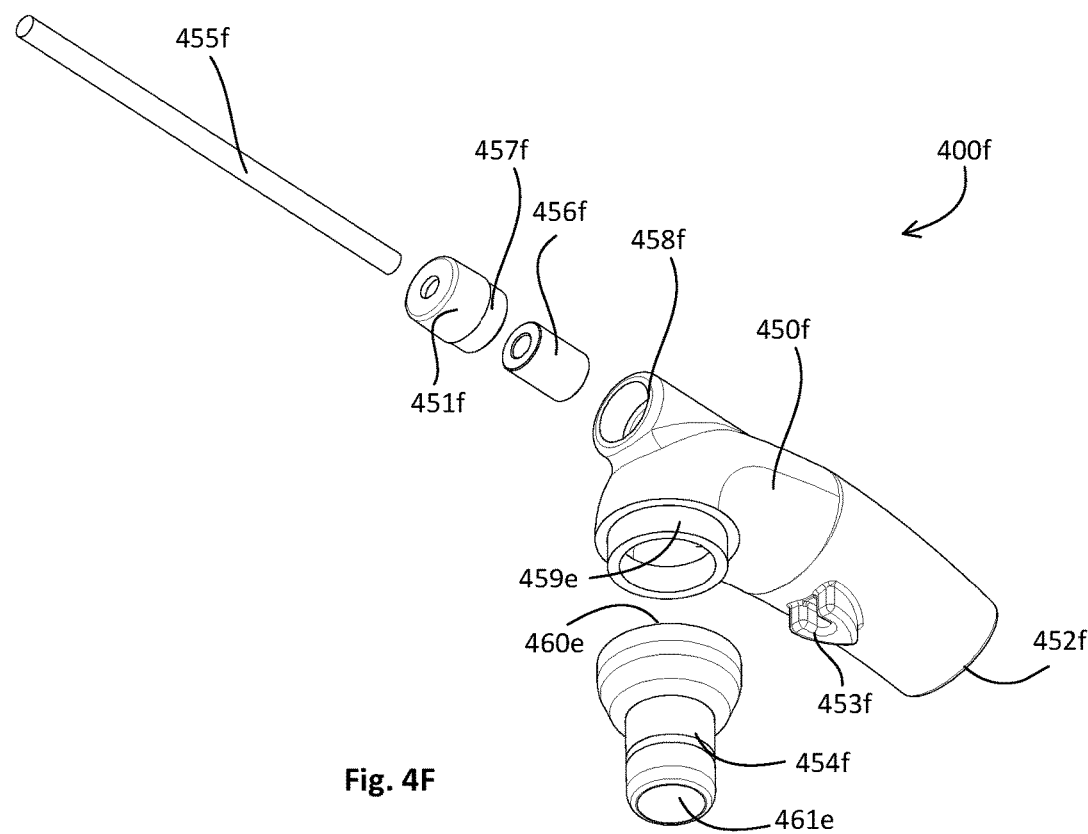
Figures 4G, 4H, 4J:
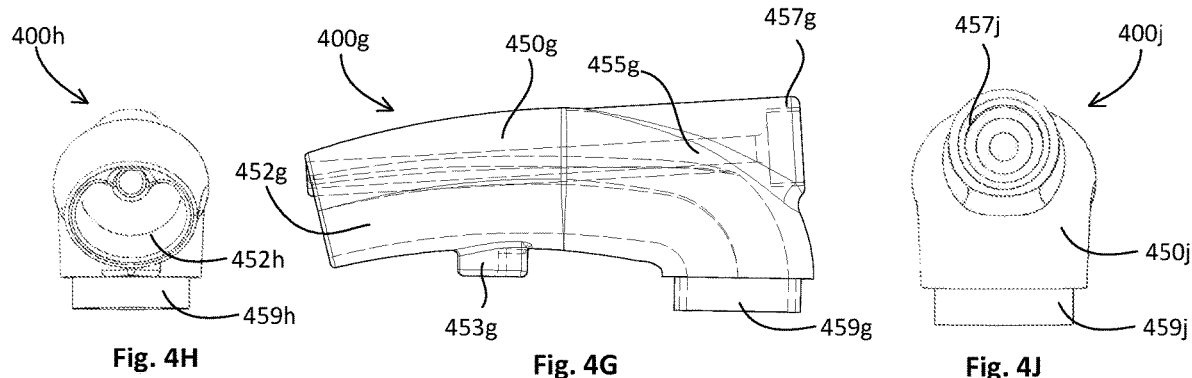
Figures 4K, 4L, 4M:
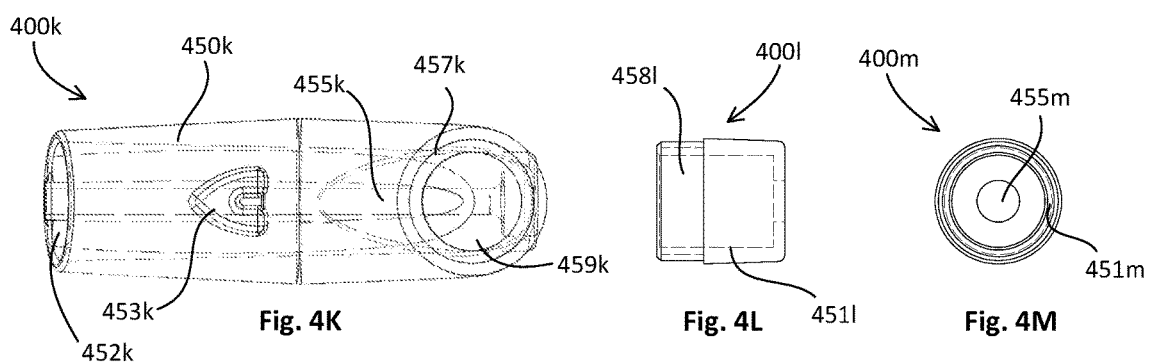
Figure 4P:
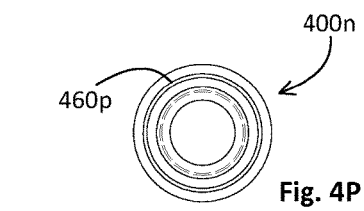
Figure 4N:
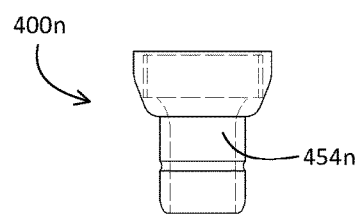
Figure 4Q:
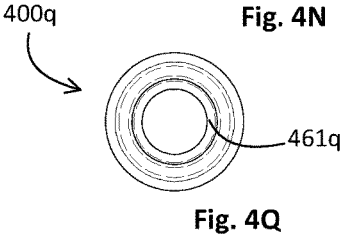
Figure 5A:
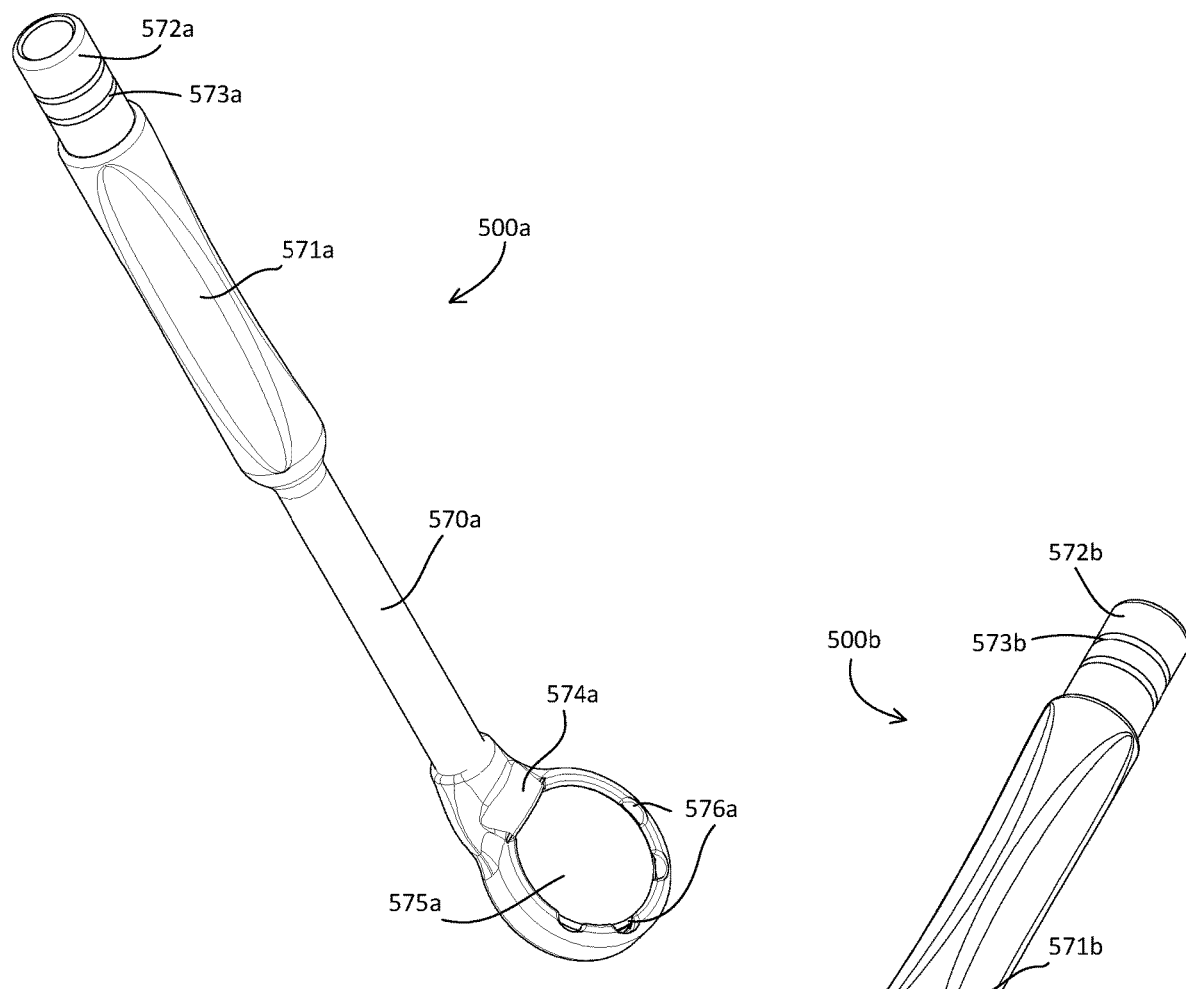
FIGS. 5A-D depict various views of an example saliva evacuation dental mirror assembly.
Figure 5B:
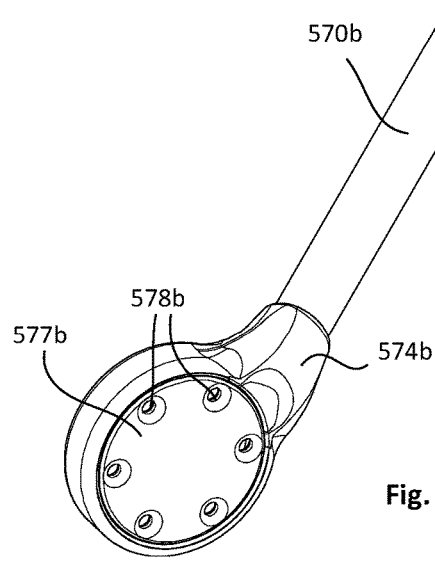
Figure 5C:
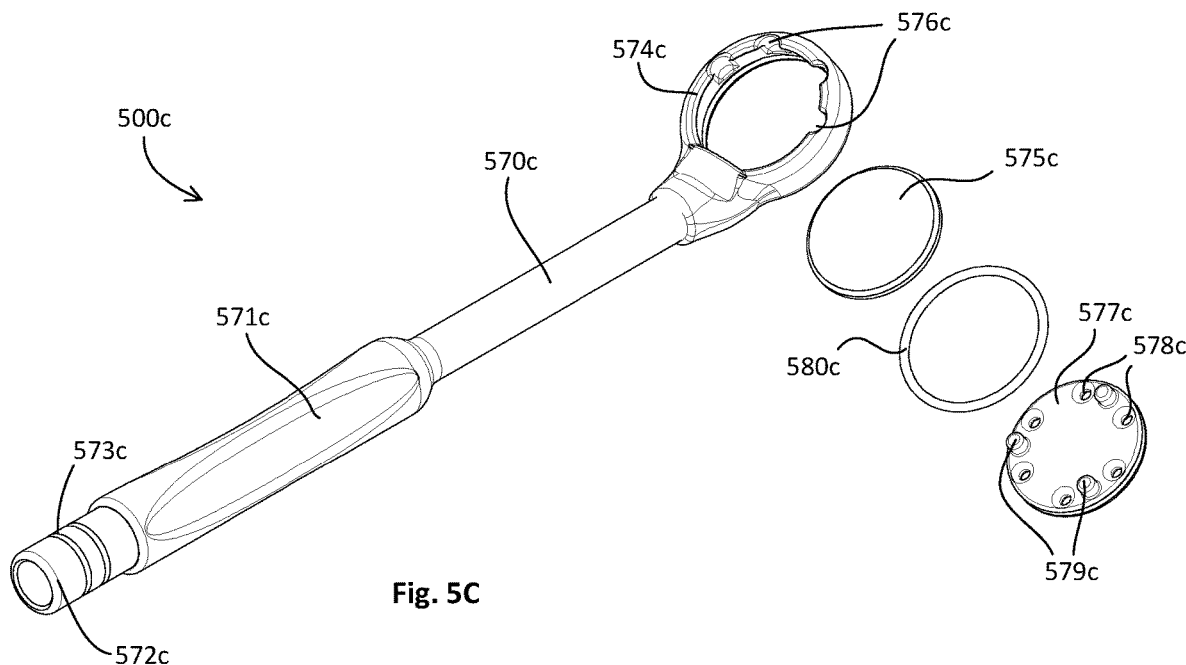
Figure 5D:
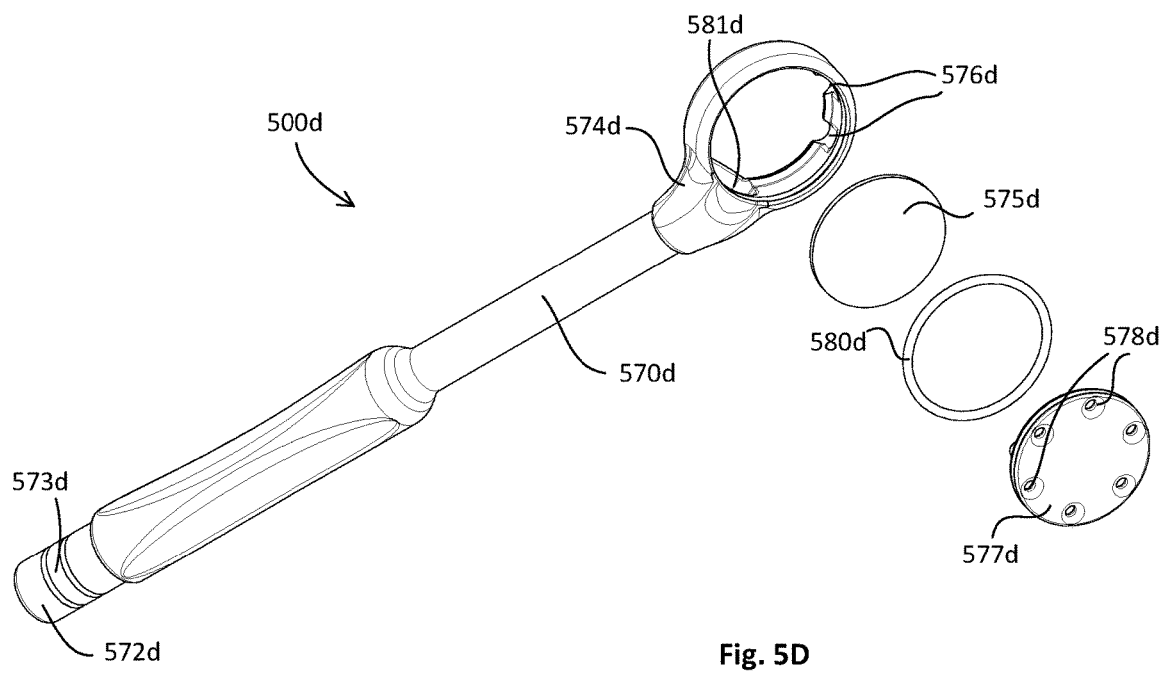

With reference to FIGS. 2A and 2B, a dental instrument assembly with illumination and/or saliva evacuation 200a,b may include a fiber optic element 222b removably connected to a dental instrument adapter 250b via, for example, a magnetic coupler 251b. The dental instrument assembly with illumination and saliva evacuation 200a,b may also include a vacuum line 223a,b removably connected to the dental instrument adapter 250b (or an evacuation mirror 270a) via, for example, a pneumatic coupling 254a,b. The vacuum line 223a,b may be connected to a vacuum source 224a,b via, for example, a valve 235a,b having a thumb operating lever 236a,b. The dental instrument assembly with illumination and saliva evacuation 200a,b may also include a wrist band 201a,b having a clasp 202a,b and a vacuum line snap in clamp 203a,b. The valve 235a,b may be similar to, for example, the valve 135 of FIG. 1. The dental instrument adapter 250b may be similar to, for example, the dental instrument adapter 150 of FIG. 1. Further details of the valve 235a,b and the dental instrument adapter 250b are described herein.

The dental instrument assembly with illumination and saliva evacuation 200a,b may further include a mouth piece 285b having at least one receptacle 287b configured to receive at least one adapter interlock 253b when the mouth piece 285b is operably engaged with the dental instrument adapter 250b. The mouth piece 285b may be similar to, for example, the mouth piece 185 of FIG. 1. Further details of the mouth piece 285b are described herein.

While the dental instrument assembly with illumination and saliva evacuation 200a,b is illustrated as having both the fiber optic element 222b and the vacuum line 223a,b connected to the adapter 250b via independent connections (i.e., the fiber optic element 222b and the vacuum line 223b may be connected to, or discounted from, the dental instrument adapter 250b independent of one another), the dental instrument assembly with illumination and saliva evacuation 200b may be used in a limited operation mode with either the fiber optic element 222b and/or the vacuum line 223b disconnected from the adapter 250b. In any event, the fiber optic element 222a,b and/or the vacuum line 223a,b may be swivalably connected to the adapter 250b such that twisting of the fiber optic element 222b and the vacuum line 223b are reduced relative to when swivable connections are not provided.

Turning to FIGS. 3A-D, a valve assembly 300a-d may include a valve body 335a-d having a rotatable barrel 337a-d removably inserted in the valve body 335a-d. The valve assembly 300a-d may be similar to, for example, the valve 135 of FIG. 1 or the valve 235 of FIG. 2. The valve assembly 300a-d may include, for example, a user thumb lever control 336a-d configured to enable user control of the valve assembly 300a-d, via a thumb of the user, when the valve assembly 300a-d is held in a respective hand of the user. The valve assembly 300a-d may include first and second barrel o-rings 346c,d configured with respective barrel annual grooves and valve body grooves such that the barrel 337a-d is linearly removably snap fit within the valve body 335a-d, rotatable and pneumatically sealed therewithin. The barrel 337a-d may include a bore having a cross section opening equal to, or greater than, a bore of an associated dental instrument adapter 150, 250. While not shown in FIGS. 3A-D, the valve assembly 300a-d may include a remote, wireless, control interconnection.

The valve assembly 300a-d may further include a vacuum source connecter 338a-d and a dental instrument connector 339a-d. As described herein, the vacuum source connecter 338a-d and/or the dental instrument connector 339a-d may be removably and/or swivably connected to the valve body 335a-d. Thus, twisting of associated vacuum lines is reduced relative to when a swivable connection is not provided. For example, the vacuum source connecter 338a-d may include a male hose engagement 340c,d and a male swivel connection 341c,d for linear snap reception within a valve body female receptacle 342c,d with o-ring 346c,d. The dental instrument connector 339a-d may include a male hose engagement 345c,d and a female swivel connection 344c,d with o-ring 346c,d for linear snap reception within a valve body male plug 343c,d.

With reference to FIGS. 4A-H, 4J-N, 4P and 4Q, dental instrument adapter 400a-h,j-n,p,q may include an adapter body 450a-g,j,k having an illumination source connection 451a-f,l,m, a vacuum source connection 454a-f,n, and a dental instrument connection 452a-f,h,g,k. The dental instrument adapter 400a-h,j-n,p,q may be similar to, for example, the dental instrument adapter 150 of FIG. 1 or the dental instrument adapter 250 of FIG. 2. The dental instrument adapter 400a-h,j-n,p,q may also include an optical element (e.g. a element, a Borosilicate Glass element, a quartz, a simax glass rod, as available from https://fdglass.com/our-products/simax-glass-tubing-rod/, a quartz element, as available from https://fdglass.com/our-products/quartz-tubing-rod/, a PMMA element, a fiber optic element, etc.) 455a-f, g,k extending, for example, from the illumination source connection 451a-f,l,m to the dental instrument connection 452a-f,h,g,k. Each end of the optical element 455a-f,g,k may be polished. Alternatively, a distal end of the optical element 455a-f,g,k may be rough to diffract associated light as the light is emitted from the optical element 455a-f,g,k. Additionally, either end of the optical element 455a-f,g,k may include a convex lens, a concave lens, etc. depending on desired light pattern desires.

Figure 7A:
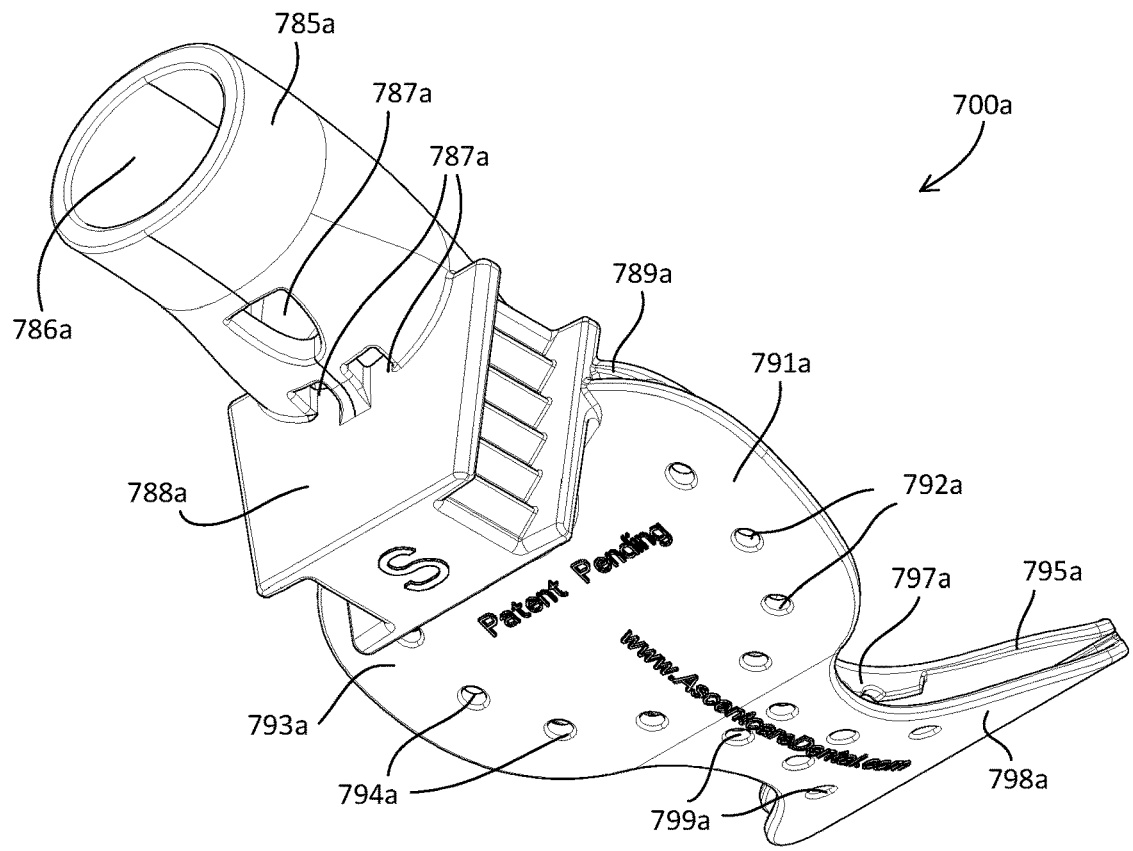
FIGS. 7A-H and 7J-L depict various views of an example mouth piece.
Figure 7B:
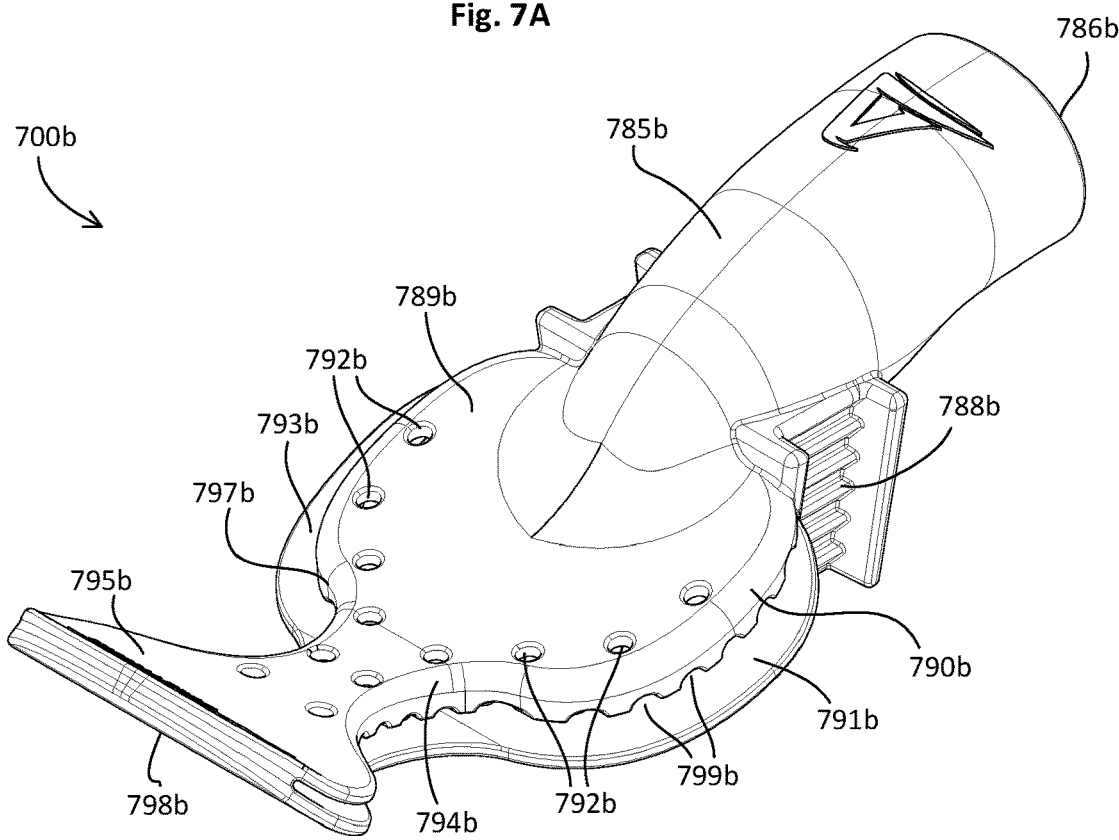
Figure 7C:
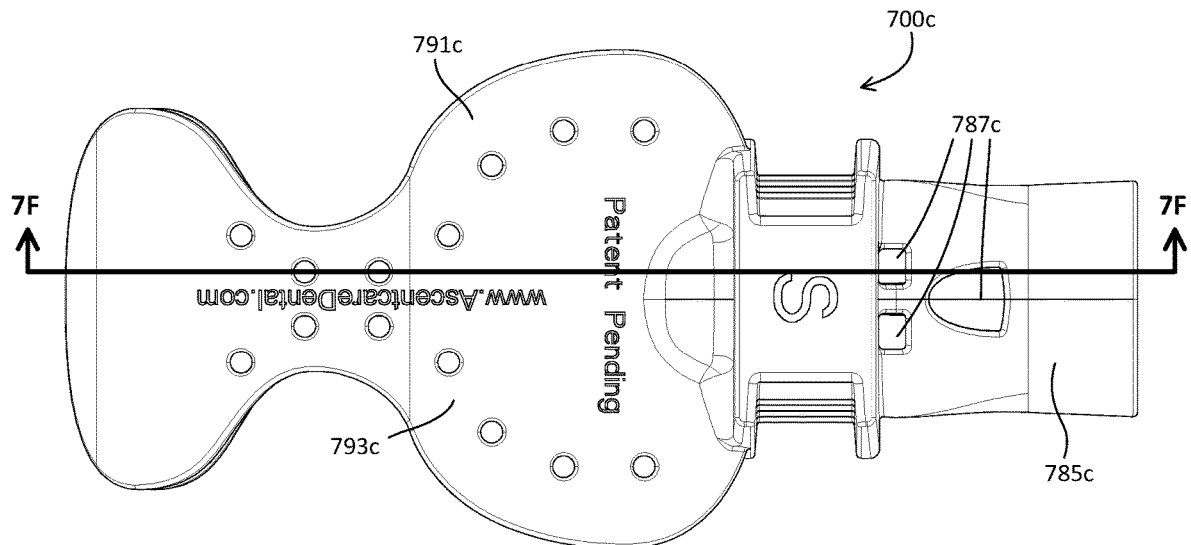
Figure 7D:
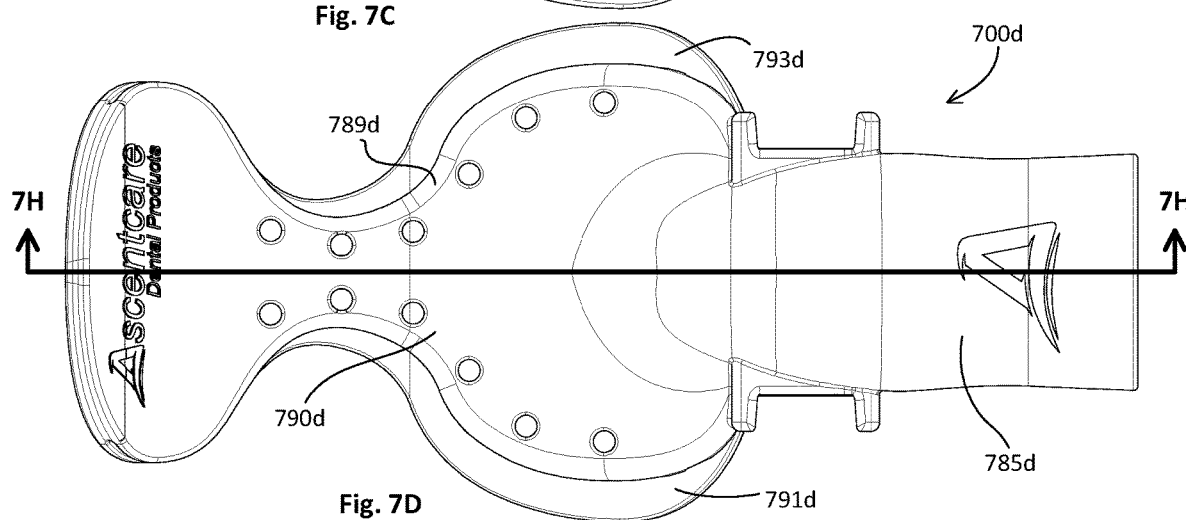
Figure 7E:
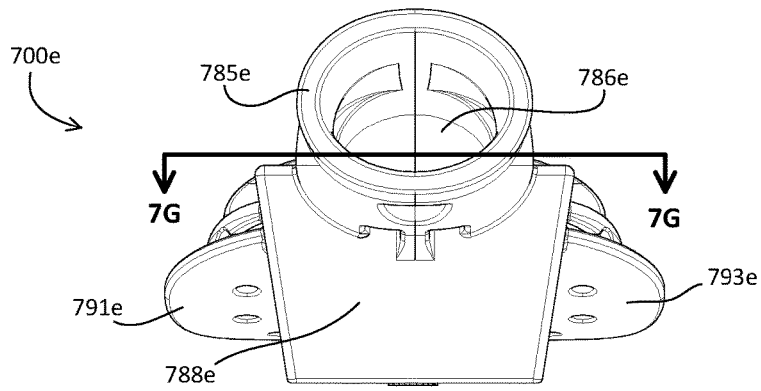

The dental instrument connection 452a-f,h,g,k may include at least one adapter interlock 453a-f,g,k configured to be received within a respective receptacle (e.g., at least one of receptacle 787a of FIG. 7A) of a removable dental instrument (e.g., mouth piece 700a-h,j-l of FIGS. 7A-H and 7J-L) when the removable dental instrument 700a-h,j-l is operably encaged with the dental instrument connection 452a-f,h,g,k. The dental instrument adapter 400a-h,j-n,p,q may also include a magnetically energetic material 456d-f.

The optical element 455a-f,g,k may be retained within the dental instrument adapter 400a-h,j-n,p,q with a silicone material (e.g., DOWSIL 734, available from the Dow Chemical Company, a clear silicone rubber, etc.). A melting point of the silicone material may be greater than 121° C. An index of refraction of the silicone material (e.g., 1.20-1.4) may be less than an index of refraction of the optical element 455a-f (e.g., 1.40-1.6). Thereby, end to end light transmission of the optical element 455a-f,g,k may be increased relative to using a silicone material with a higher index of refraction.

The illumination source connection 451a-f,l,m may include a cup shaped cap with male threaded portion 458e,f,l to be received within an adapter body female threaded portion 457e,f, g,j. The vacuum source connection 454a-f,n may include a male linear snap in portion 461e,f,q and a female threaded receptacle 460e,f,p configured to receive an adapter body male threaded portion 459e,f,h,g,j,k. Additionally, or alternatively, the cup shaped cap with male threaded portion 458e,f and/or the vacuum source connection 454a-f,n may be fixed to the dental instrument adapter body 450a-f,g,j,k via any mechanism capable of being autoclaved without disengagement (e.g., adhesive, friction spin welding, electric welding, Scotch-Weld Epoxy adhesive 2216, available from 3M Corporation, etc.). The dental instrument adapter body 450a-f,g,j,k, the cup shaped cap with male threaded portion 458e,f and/or the vacuum source connection 454a-f,n may be made of aluminum. Forming the dental instrument adapter 400a-h,j-n,p,q of the three individual pieces (e.g., the dental instrument adapter body 450a-f,g,j,k, the cup shaped cap with male threaded portion 458e,f, and the vacuum source connection 454a-f,n) enables machining a bore through the dental instrument adapter body 450a-f, g,j,k free of any discontinuities in associated bore walls. The bore through the dental instrument adapter body 450a-f,g,j,k may include a cross section area greater than, or equal to, a bore through an associated valve 135, 235, 400a-d. The dental instrument adapter body 450a-f,g,j,k, the cup shaped cap with male threaded portion 458e,f, and the vacuum source connection 454a-f,n may be made of aluminum.

Turning to FIGS. 5A-D, a saliva evacuation dental mirror assembly 500a-d may include tubular body 570a-d having a hand-hold portion 571a-d and a male vacuum source connection 572a-d with circumferentially extending o-ring groove(s) 573a-d (i.e., having two or more linearly spaced o-ring grooves may accommodate various female receptacles on, for example, an associated valve, vacuum hose, etc.). The saliva evacuation dental mirror assembly 500a-d may also include head 574a-d, having a plurality of openings 576a-d extending around a perimeter, connected to a distal end of the tubular body 570a-d. The head 574a-d is configured to receive a dental mirror element 575a-d, an o-ring 580c,d, and a bottom 577b-d having a plurality of apertures 578b-d and alignment features 579c. The tubular body 570a-d, the hand-hold portion 571a-d, the male vacuum source connection 572a-d, the head 574a-d, and/or the bottom 577b-d may be made of aluminum.

Figure 6:
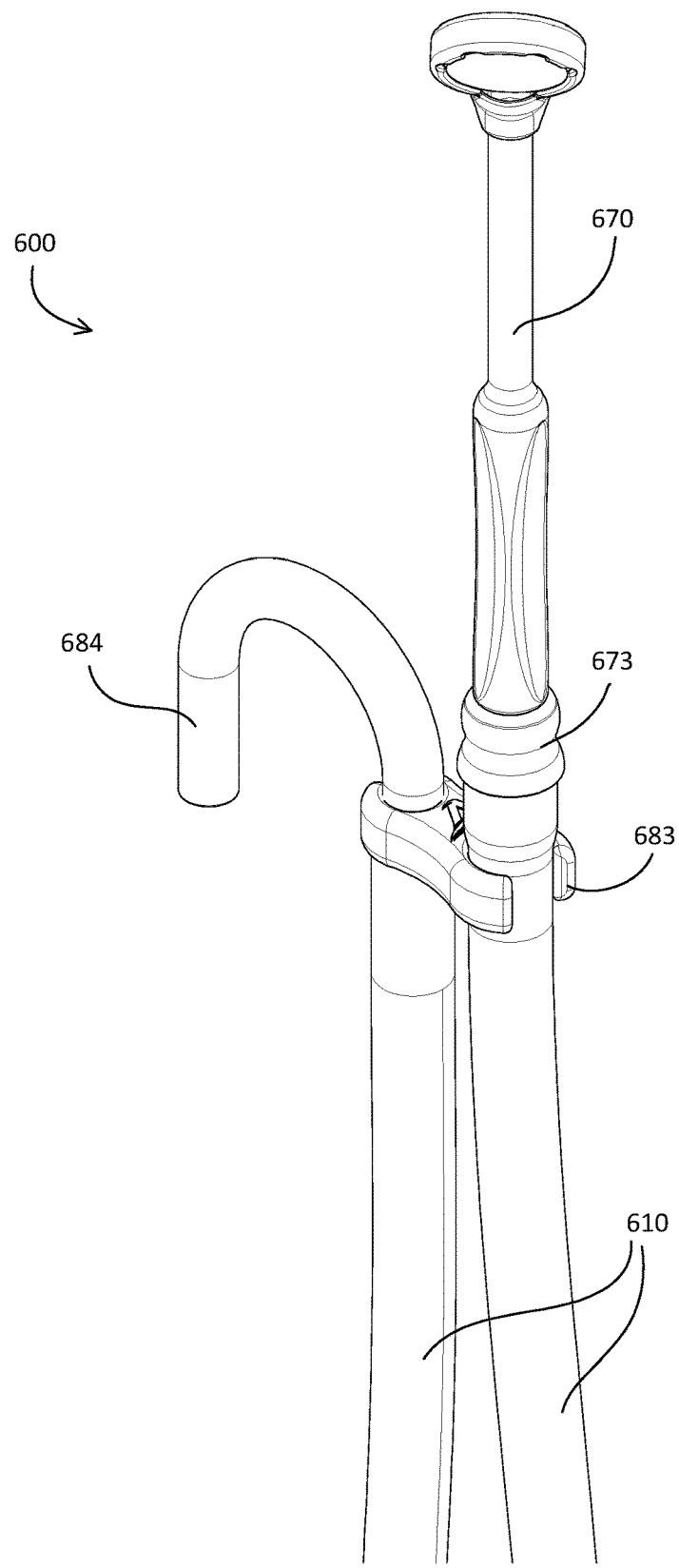
FIG. 6 depicts an example dental saliva evacuation mirror and saliva evacuation assembly.

With reference to FIG. 6, a dental saliva evacuation mirror and saliva evacuation assembly 600 may include a saliva evacuation dental mirror assembly 670 connected to a vacuum source 610 via, for example, a swivable linear snap in connecter 671. The dental saliva evacuation mirror and saliva evacuation assembly 600 may also include a saliva ejection tube 684 connected to the vacuum source 610. The dental saliva evacuation mirror and saliva evacuation assembly 600 may be similar to, for example, the dental saliva evacuation mirror and saliva evacuation assembly 184 of FIG. 1. The saliva evacuation dental mirror assembly 670 may be similar to, for example, the saliva evacuation dental mirror assembly 500a-d of FIGS. 5A-D.

Turning to FIGS. 7A-H and 7J-L, a dental instrument (i.e., a mouth piece) 700a-h,j-l may include a body portion 785a-e having a saliva ejection port 786a-e and at least one receptacle 787a,c configured to receive a respective adapter interlock (e.g., adapter interlock 453a-f) when the mouth piece is operably encaged with, for example, a dental instrument connection. The mouth piece 700a-h,j-l may be similar to, for example, the mouth piece 185 of FIG. 1 or the mouth piece 285 of FIG. 2. The mouth piece 700a-h,j-l may include an integral bite block 788a,b,e. The mouth piece 700a-h,j-l may be injection molded of silicon (e.g., Silicon, as available from Doneson DSA-7140, etc.)

The mouth piece 700a-h,j-l may include a first front flap 789b, a second front flap 790b, a first rear flap 791a, and a second rear flap 793a. A front perimeter around an outer edge of the first front flap 789b and an outer edge of the second front flap 790b may be less than a rear perimeter around an outer edge of the first rear flap 791a and an outer edge of the second rear flap 793a. This configuration may, for example, result in improved dental patient comfort, improved saliva evacuation, lower vacuum induced noise, etc.

Figure 7F:
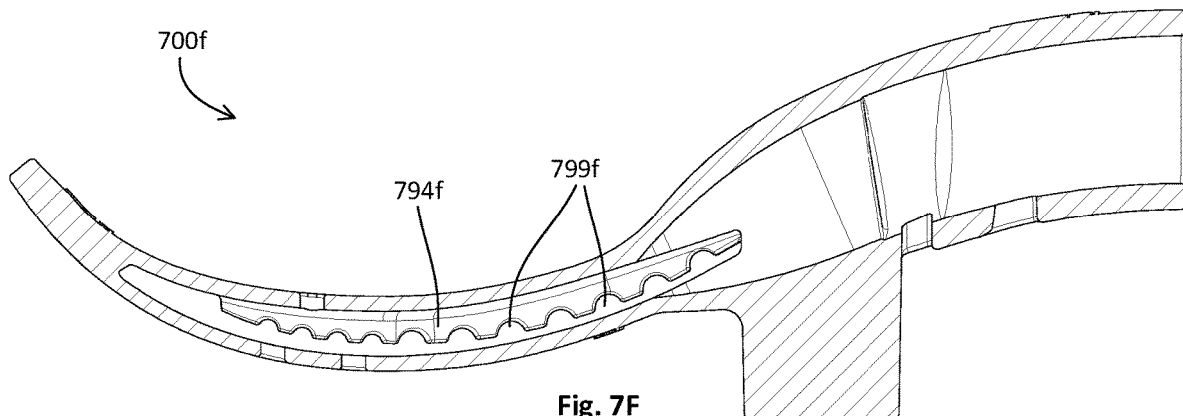
Figure 7G:
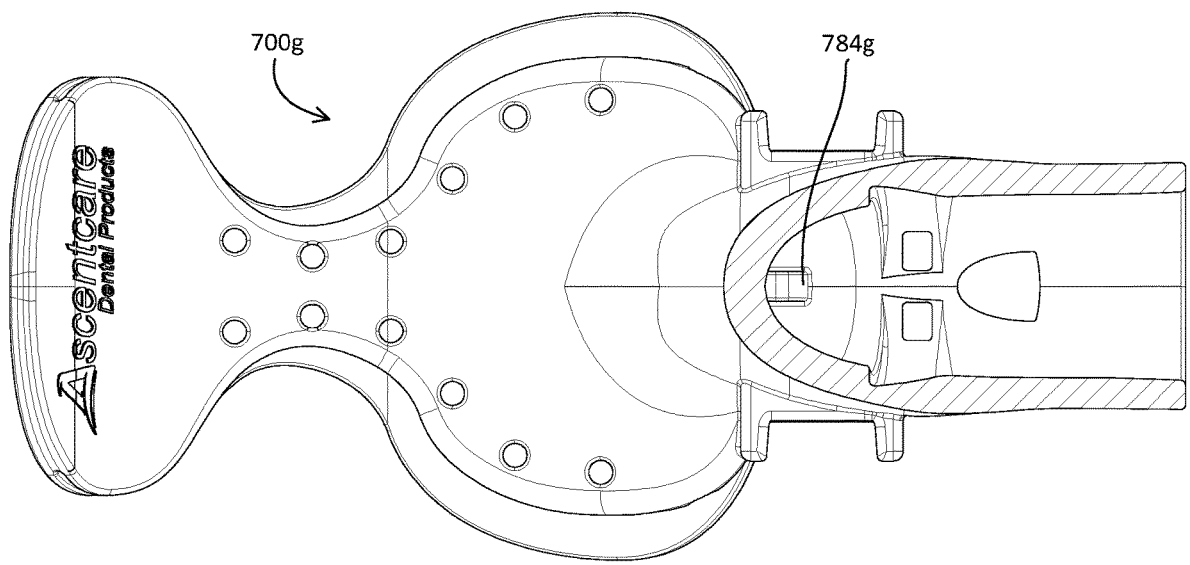
Figure 7H:
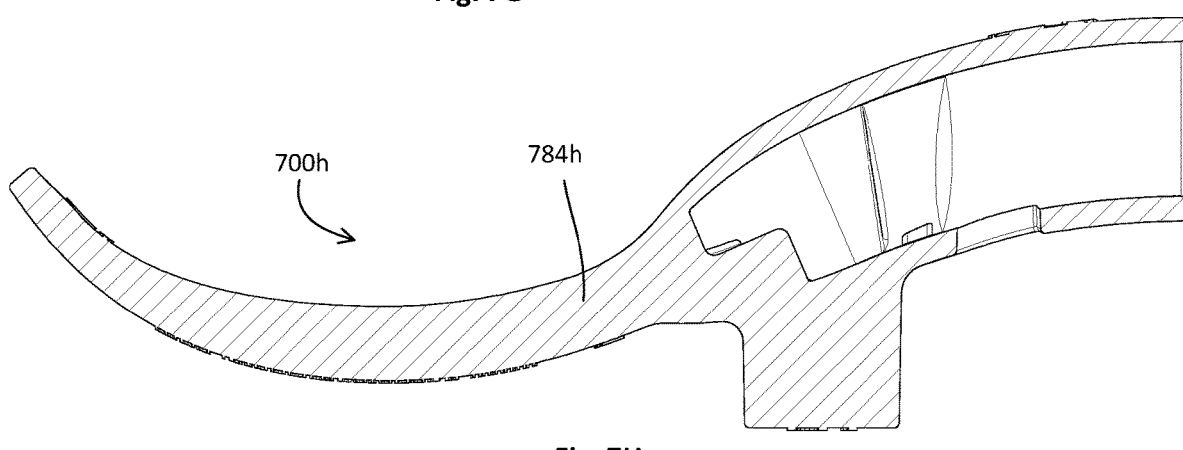
Figure 7J:
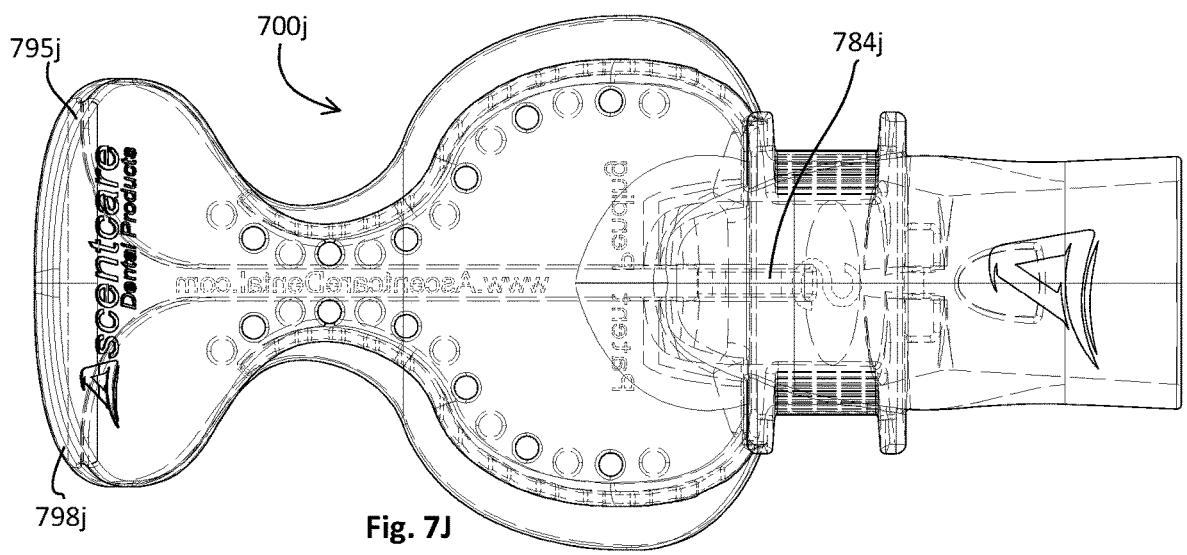
Figure 7K:
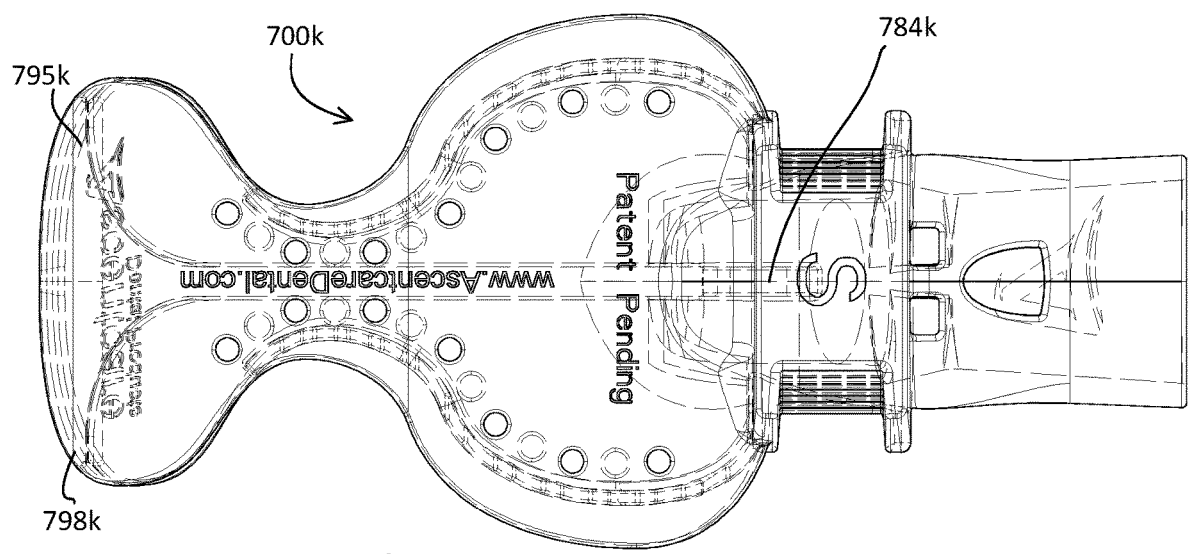
Figure 7L:
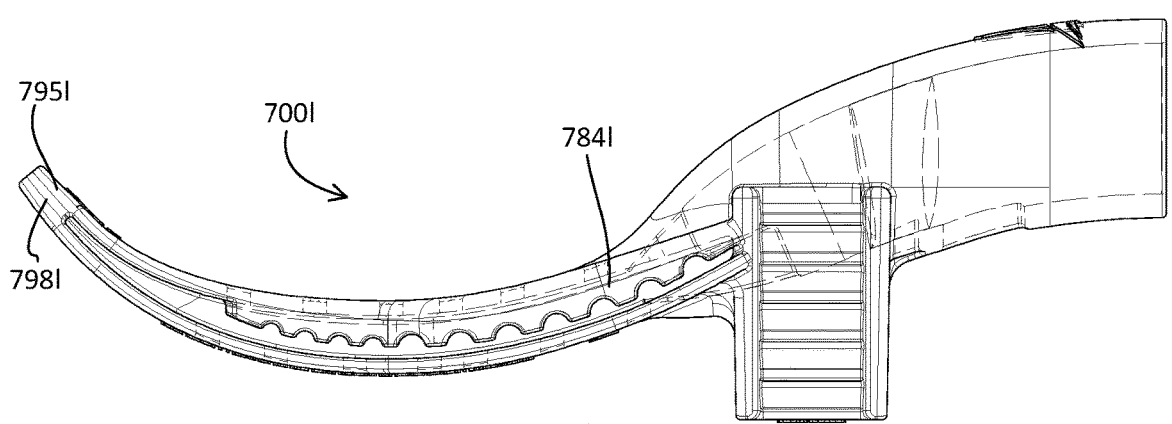

An outer edge of the first front flap 789b and an outer edge of the second front flap 790b may include a respective sidewall 794b,f having a non-planar bottom 799b,f. The first front flap 789b, the second front flap 790b, the first rear flap 791a, and the second rear flap 793a may include a plurality of apertures 792b, 794a, 799b. At least a portion of a distal end 795a,b of the first front flap 789b and the second front flap 790b may be connected to at least a portion of a distal end 798a,b of the first rear flap 791a and the second rear flap 793a. As best illustrated in FIGS. 7J-L, the connection of the distal ends 795a,b, 798a,b may define a distal end of a core 784a,h,j-l. An inner edge of the first front flap 789b may be connected with an inner edge of the second front flap 790b via a core 784g,h,j-l. An inner edge of the first rear flap 791a may be connected with an inner edge of the second rear flap 793a via the core 784g,h,j-l. The core 784g,h,j-l may include a first side wall extending between the first front flap 789b and the first rear flap 791a. The core 784g,h,j-l may include a second side wall extending between the second front flap 790b and the second rear flap 793a. A distance between the first side wall and the second side wall may increase along the core 784g,h,j-l starting from the exhaust port 786a,b of the mouth piece 700a-h,j-l to a distal end 795j-l of the mouth piece 700a-h,j-l. The core may function as a light pipe to transmit light from, for example, an optical element 455a-f (i.e., a distal end of an optical element 455a-f may be generally aligned with a proximal end of the core 784g,h,j-l when an associated mouth piece 700a-h,j-l is engaged with, for example, a dental instrument adapter 400a-h,j-n,p,q. A cross section of the first side wall and/or the second side wall may define a continuous curve with respect to a corresponding inner surface of the respective top flap and/or bottom flap. Alternatively, a cross section of the first side wall and/or the second side wall may define a fileted curve.

In any event, the specific the mouth piece 700a-h,j-l shapes may improve sterilization ability, improved ability to resist debris buildup, reduced vacuum induced noise, etc. The shape of the core 784g,h,j-l (both plan and profile) may also result in improved structural performance (i.e., a dental patient's cheek may be pushed outward by the distal end of the mouth piece 700a-h,j-l.

The shape of the core 784g,h,j-l as best illustrated in FIGS. 7J-L may, for example, improve mouth piece 700a-h,j-l cleaning, sterilization, saliva evacuation, vacuum induced noise, etc. The section view of FIG. 7F is taken along the section line 7F-7F of FIG. 7C. The section view of FIG. 7H is taken along the section line 7H-7H of FIG. 7D. The section view of FIG. 7G is taken along the section line 7G-7G of FIG. 7E.

It will be understood by one having ordinary skill in the art that construction of the described invention and other components is not limited to any specific material. Other exemplary embodiments of the invention disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

For purposes of this disclosure, the term "operably connected" generally means that one component functions with respect to another component, even if there are other components located between the first and second component, and the term "operable" defines a functional relationship between components.

It is also important to note that the construction and arrangement of the elements of the invention as shown in the exemplary embodiments is illustrative only. Although only a few embodiments of the present innovations have been described in detail in this disclosure, those skilled in the art who review this disclosure will readily appreciate that, unless otherwise described, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or coupler or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating positions, and arrangement of the desired and other exemplary embodiments without departing from the spirit of the present innovations.

It will be understood that any described processes or steps within described processes may be combined with other disclosed processes or steps to form structures within the scope of the present invention. The exemplary structures and processes disclosed herein are for illustrative purposes and are not to be construed as limiting.

It is also to be understood that variations and modifications can be made on the aforementioned structures and methods without departing from the concepts of the present invention, and further it is to be understood that such concepts are intended to be covered by the following claims unless these claims by their language expressly state otherwise.

What is claimed is:

1. A dental instrument assembly, comprising:
a dental instrument adapter having an illumination source connection, a vacuum source connection, and a dental instrument connection, wherein the vacuum source connection is swivably connectable to a vacuum source, wherein the illumination source connection is swivably connectable to an illumination source independent of the vacuum source connection to the vacuum source, and wherein the dental instrument connection is connectable to a removable dental instrument having at least one receptacle configured to receive a respective adapter interlock of the dental instrument connection; and
a dental instrument connected to the dental instrument adapter, wherein the dental instrument includes at least one receptacle configured to receive a respective adapter interlock of a dental instrument adapter, wherein the dental instrument is a mouth piece having a first front flap, a second front flap, a first rear flap, and a second rear flap, wherein a front perimeter around an outer edge of the first front flap and an outer edge of the second front flap is less than a rear perimeter around an outer edge of the first rear flap and an outer edge of the second rear flap, wherein an inner edge of the first front flap is connected with an inner edge of the second front flap via a core, wherein an inner edge of the first rear flap is connected with an inner edge of the second rear flap via the core, wherein the core includes a first side wall extending between the first front flap and the first rear flap, wherein the core includes a second side wall extending between the second front flap and the second rear flap, and wherein a distance between the first side wall and the second side wall increases along the core starting from an exhaust port of the mouth piece to a distal end of the mouth piece.

2. The dental instrument assembly of claim 1, wherein the removable dental instrument is a mouth piece.

3. The dental instrument assembly of claim 2, wherein the mouth piece includes at least one receptacle, wherein the dental instrument connection includes at least one adapter interlock configured to be received within the at least one receptacle when the mouth piece is operably encaged with the dental instrument connection.

4. The dental instrument assembly of claim 1, wherein the illumination source connection includes a magnetically energetic material.

5. The dental instrument assembly of claim 1, wherein the dental instrument adapter includes a glass rod extending from the illumination source connection to the dental instrument connection.

6. The dental instrument assembly of claim 1, further comprising:
a pneumatic valve connected between the vacuum source connection and the vacuum source.

7. The illuminated dental instrument assembly of claim 6, further comprising:
a vacuum line connected between the pneumatic valve and the vacuum source connection such that the pneumatic valve can be operably connected to the dental instrument adapter remote from a head of a dental patient when the removable dental instrument is oriented in an in-use orientation.

8. A dental instrument assembly, comprising:
a dental instrument having at least one receptacle configured to receive a respective adapter interlock of a dental instrument adapter, wherein the dental instrument is a mouth piece having a first front flap, a second front flap, a first rear flap, and a second rear flap, wherein a front perimeter around an outer edge of the first front flap and an outer edge of the second front flap is less than a rear perimeter around an outer edge of the first rear flap and an outer edge of the second rear flap, wherein an inner edge of the first front flap is connected with an inner edge of the second front flap via a core, wherein an inner edge of the first rear flap is connected with an inner edge of the second rear flap via the core, wherein the core includes a first side wall extending between the first front flap and the first rear flap, wherein the core includes a second side wall extending between the second front flap and the second rear flap, and wherein a distance between the first side wall and the second side wall increases along the core starting from an exhaust port of the mouth piece to a distal end of the mouth piece.

9. The dental instrument assembly of claim 8, wherein the core is configured as a light pipe.

10. The dental instrument assembly of claim 8, wherein an outer edge of the first front flap and an outer edge of the second front flap includes a respective sidewall having a non-planar bottom.

11. The dental instrument assembly of claim 8, wherein the mouth piece includes an integral bite block.

12. A dental instrument assembly, comprising:
a dental instrument having an integral bite block, a core, and at least one receptacle configured to receive a respective adapter interlock of a dental instrument adapter, wherein the dental instrument is a mouth piece having a first front flap, a second front flap, a first rear flap, and a second rear flap, wherein a front perimeter around an outer edge of the first front flap and an outer edge of the second front flap is less than a rear perimeter around an outer edge of the first rear flap and an outer edge of the second rear flap, wherein the core includes a first side wall extending between the first front flap and the first rear flap, wherein the core includes a second side wall extending between the second front flap and the second rear flap, and wherein a distance between the first side wall and the second side wall increases along the core starting from an exhaust port of the mouth piece to a distal end of the mouth piece.

13. The dental instrument assembly of claim 12, wherein the mouth piece includes at least one receptacle configured to receive at least one adapter interlock within the at least one receptacle when the mouth piece is operably encaged with the dental instrument adaptor.

14. The dental instrument assembly of claim 12, wherein an inner edge of the first front flap is connected with an inner edge of the second front flap via a core.

15. The dental instrument assembly of claim 14, wherein an inner edge of the first rear flap is connected with an inner edge of the second rear flap via the core.

16. The dental instrument assembly of claim 12, wherein an outer edge of the first front flap and an outer edge of the second front flap includes a respective sidewall having a non-planar bottom.

* * * * *